United States Patent
Woods

(10) Patent No.: US 12,072,889 B2
(45) Date of Patent: Aug. 27, 2024

(54) INTERMEDIATE DATA OBJECTS AND USES THEREOF

(71) Applicant: UNITED STATES GOVERNMENT AS REPRESENTED BY THE DEPARTMENT OF VETERANS AFFAIRS, Washington, DC (US)

(72) Inventor: Anne S Woods, San Francisco, CA (US)

(73) Assignee: UNITED STATES GOVERNMENT AS REPRESENTED BY THE DEPARTMENT OF VETERANS AFFAIRS, Washington, DC (US)

(*) Notice: Subject to any disclaimer, the term of this patent is extended or adjusted under 35 U.S.C. 154(b) by 279 days.

(21) Appl. No.: 17/290,933

(22) PCT Filed: Nov. 4, 2019

(86) PCT No.: PCT/US2019/059696
§ 371 (c)(1),
(2) Date: May 3, 2021

(87) PCT Pub. No.: WO2020/093056
PCT Pub. Date: May 7, 2020

(65) Prior Publication Data
US 2021/0374142 A1 Dec. 2, 2021

Related U.S. Application Data

(60) Provisional application No. 62/755,451, filed on Nov. 3, 2018.

(51) Int. Cl.
G06F 16/2455 (2019.01)
G06F 16/2458 (2019.01)
G16H 10/60 (2018.01)

(52) U.S. Cl.
CPC .... G06F 16/24561 (2019.01); G06F 16/2474 (2019.01); G06F 16/2477 (2019.01); G16H 10/60 (2018.01)

(58) Field of Classification Search
CPC .......................... G06F 16/285; G06F 16/24561
USPC ........................................................ 707/769
See application file for complete search history.

(56) References Cited

U.S. PATENT DOCUMENTS

| 2011/0112860 | A1* | 5/2011 | Kehr | G16H 20/10 705/2 |
| 2012/0163132 | A1* | 6/2012 | Downey | A61J 7/0481 368/10 |
| 2014/0297312 | A1 | 10/2014 | Bangera et al. | |

* cited by examiner

Primary Examiner — Hung T Vy
(74) Attorney, Agent, or Firm — Ballard Spahr LLP

(57) ABSTRACT

An intermediate data object is described that bridges source data to analysis-ready variables (ARVs).

25 Claims, 16 Drawing Sheets

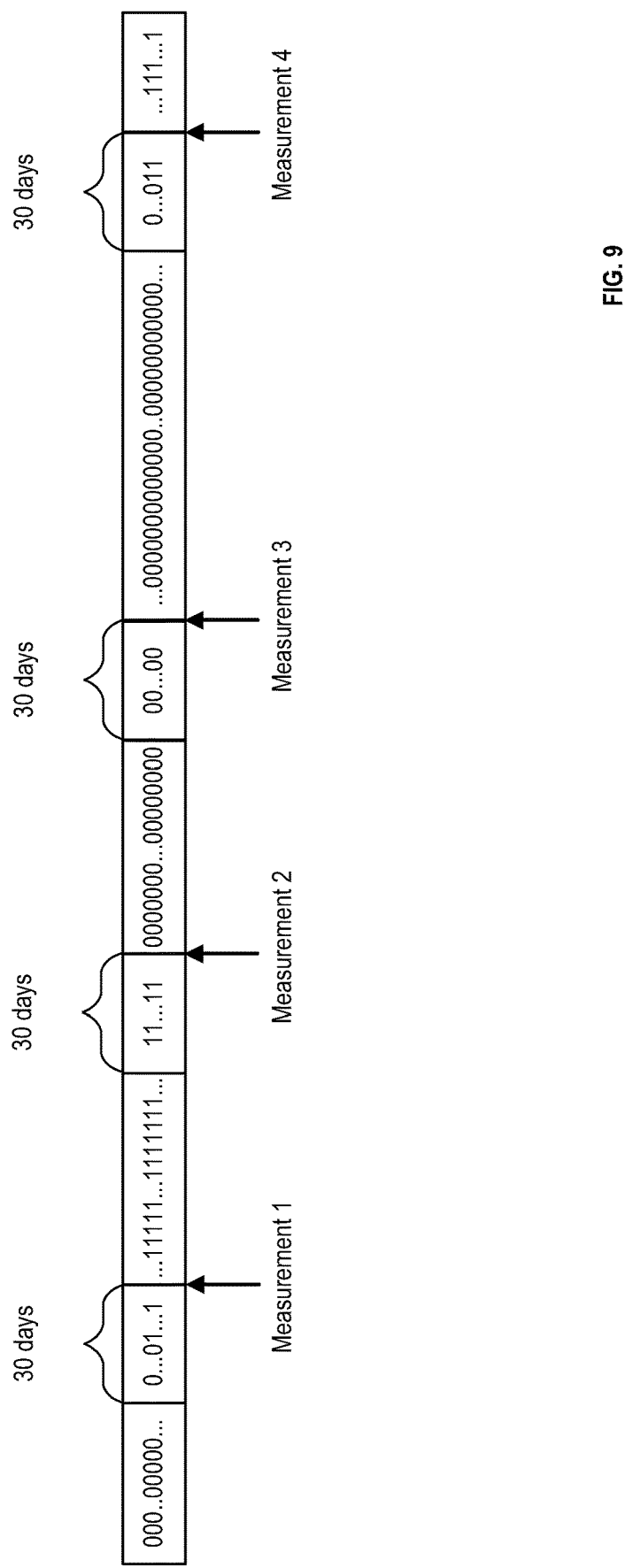

INTERMEDIATE DATA OBJECTS AND USES THEREOF

CROSS-REFERENCE TO RELATED APPLICATIONS

This is a U.S. National Phase Application of International Application No. PCT/US2019/059696, filed Nov. 4, 2019, which claims the benefit of U.S. Provisional Patent Application No. 62/755,451, filed Nov. 3, 2018, both of which are hereby incorporated by reference herein in their entireties.

BACKGROUND

The expanding adoption of Electronic Health Records (EHR) continues to create treasure troves of data for healthcare research. Frequently they are represented as time-stamped records stored in data warehouses and databases. Large databases, such as an EHR database for the Veterans Administration, have relevant health data distributed among many (e.g., hundreds) of different tables. There are many different types of health data, often time-stamped. These time-stamped data may be considered temporal snapshots of various health status states. Research on these HER data sometimes desires an analysis of the health status states themselves but the states are not easily accessed directly from the EHR data.

Mining these data requires first extracting, combining, and filtering large amounts of individual records from multiple tables. Next, analysis-ready variables (ARVs) are derived and arranged into datasets suitable for statistical analysis. This step requires writing custom computer codes to manipulate EHR records and is often dynamic and iterative. Analysis approach may require specific formulation of information contained in an ARV such as level of discretization, being time-invariant vs time-varying, values conditioned on or independent of other variables. The best choice may not be immediately obvious and require iterative exploration. Furthermore, research teams making use of the same or related ARVs typically repeat these data preparation tasks individually. The time-consuming nature of creating ARVs from EHR records can hinder thorough examination of the data.

SUMMARY

It is to be understood that both the following general description and the following detailed description are exemplary and explanatory only and are not restrictive. A method is described comprising: determining data values of a set of events stored in one or more databases, wherein the set of events comprises a series of values indicative of one or more occurrences or non-occurrences of an event obtained at successive times, generating an intermediate data structure associated with the event, determining that each data value of the sequence of events indicates an occurrence of the event or a non-occurrence of the event, representing, in the intermediate data structure, data values of the sequence of events that indicate the occurrence of the event with a first symbol, and representing, in the intermediate data structure, data values of the sequence of events that indicate the non-occurrence of the event with a second symbol, wherein the intermediate data structure maintains an order of the first symbols and the second symbols based on the successive times of the sequence of events.

A method is described comprising determining data values of a sequence of events stored in one or more databases, wherein the sequence of events comprises a series of values indicative of one or more occurrences or non-occurrences of an event obtained at successive times and generating an intermediate data structure, wherein the intermediate data structure comprises a string of symbols, wherein the string of symbols comprises one or more symbols, each symbol indicative of an occurrence of the event or a non-occurrence of the event, wherein the string of symbols maintains an order of the first symbols and the second symbols based on the successive times of the sequence of events.

A method is described comprising determining values of a sequence of data stored in one or more databases, determining a data value of the sequence of data, and representing, in an intermediate data structure, a symbol indicating characters of the data value.

A method is described comprising determining values of a sequence of data stored in one or more databases, determining a data value of the sequence of data, generating a plurality of intermediate data structures, wherein one intermediate data structure is generated for each character of the data value, and representing, in each of the plurality of intermediate data structures, a symbol indicating the successive characters of the data value.

A method is described comprising identifying a set of data values responsive to a query of one or more databases with the set of data values indicative of the presence or non-presence of one or more relationships, and arranging the set of data values into a set of two or more intermediate data objects with each intermediate data object having a sequence of symbols, each of the symbols having an imputed unique key based upon a position of the symbol within its associated intermediate data object wherein each intermediate data object shares the imputed unique keys for related positions of the symbols in each particular intermediate data object.

A method is described for preparing of a set of time-stamped data reflecting state-based parameters of a system. The time-stamped data are inputted into a database having a plurality of tables. The data may be processed to generate a sequence of symbols that represent one or more of the state-based parameters of the system thereby allowing an analysis of the set of sequences to serve as a proxy for an analysis of the set of time-stamped data without direct queries of the plurality of tables.

This summary is not intended to identify critical or essential features of the disclosure, but merely to summarize certain features and variations thereof. Other details and features will be described in the sections that follow.

BRIEF DESCRIPTION OF THE DRAWINGS

FIG. 9 shows an example of a time-varying covariate.

DETAILED DESCRIPTION

Figure 1:
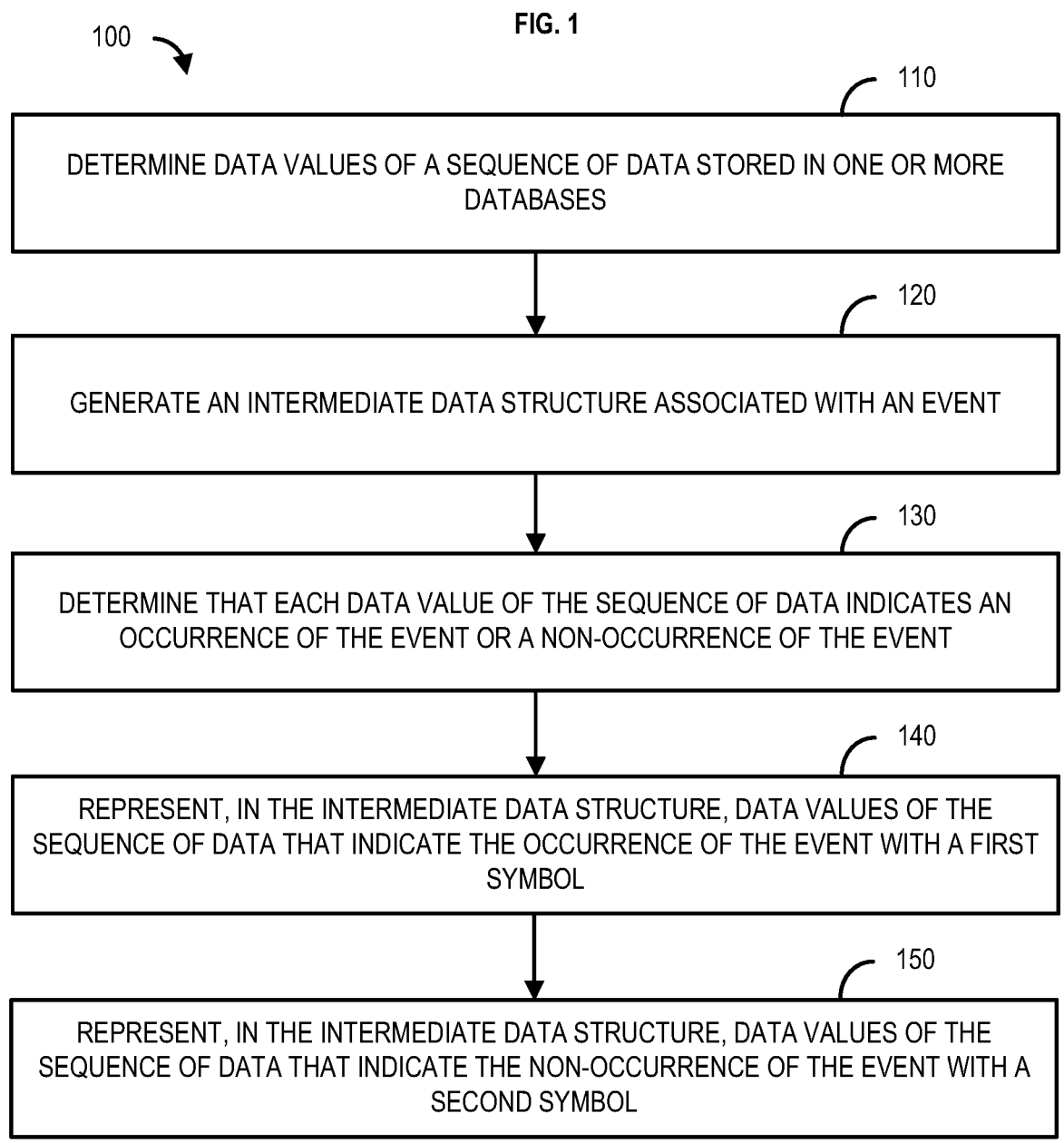
FIG. 1 shows an example method.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another configuration includes from the one particular value and/or to the other particular value. When values are expressed as approximations, by use of the antecedent "about," it will be understood that the particular value forms another configuration. It will be further understood that the endpoints of each of the ranges are significant both in relation to the other endpoint, and independently of the other endpoint.

"Optional" or "optionally" means that the subsequently described event or circumstance may or may not occur, and that the description includes cases where said event or circumstance occurs and cases where it does not.

Throughout the description and claims of this specification, the word "comprise" and variations of the word, such as "comprising" and "comprises," means "including but not limited to," and is not intended to exclude other components, integers or steps. "Exemplary" means "an example of" and is not intended to convey an indication of a preferred or ideal configuration. "Such as" is not used in a restrictive sense, but for explanatory purposes.

It is to be understood that when combinations, subsets, interactions, groups, etc. of components are described that, while specific reference of each various individual and collective combinations and permutations of these may not be explicitly described, each is specifically contemplated and described herein. This applies to all parts of this application including, but not limited to, steps in described methods. Thus, if there are a variety of additional steps that may be performed it is understood that each of these additional steps may be performed with any specific configuration or combination of configurations of the described methods.

As will be appreciated by one skilled in the art, hardware, software, or a combination of software and hardware may be implemented. Furthermore, a computer program product on a computer-readable storage medium (e.g., non-transitory) having processor-executable instructions (e.g., computer software) embodied in the storage medium. Any suitable computer-readable storage medium may be utilized including hard disks, CD-ROMs, optical storage devices, magnetic storage devices, memresistors, Non-Volatile Random Access Memory (NVRAM), flash memory, or a combination thereof.

Throughout this application reference is made to block diagrams and flowcharts. It will be understood that each block of the block diagrams and flowcharts, and combinations of blocks in the block diagrams and flowcharts, respectively, may be implemented by processor-executable instructions. These processor-executable instructions may be loaded onto a general purpose computer, special purpose computer, or other programmable data processing apparatus to produce a machine, such that the processor-executable instructions which execute on the computer or other programmable data processing apparatus create a device for implementing the functions specified in the flowchart block or blocks.

These processor-executable instructions may also be stored in a computer-readable memory that may direct a computer or other programmable data processing apparatus to function in a particular manner, such that the processor-executable instructions stored in the computer-readable memory produce an article of manufacture including processor-executable instructions for implementing the function specified in the flowchart block or blocks. The processor-executable instructions may also be loaded onto a computer or other programmable data processing apparatus to cause a series of operational steps to be performed on the computer or other programmable apparatus to produce a computer-implemented process such that the processor-executable instructions that execute on the computer or other programmable apparatus provide steps for implementing the functions specified in the flowchart block or blocks.

Accordingly, blocks of the block diagrams and flowcharts support combinations of devices for performing the specified functions, combinations of steps for performing the specified functions and program instruction means for performing the specified functions. It will also be understood that each block of the block diagrams and flowcharts, and combinations of blocks in the block diagrams and flowcharts, may be implemented by special purpose hardware-based computer systems that perform the specified functions or steps, or combinations of special purpose hardware and computer instructions.

This detailed description may refer to a given entity performing some action. It should be understood that this language may in some cases mean that a system (e.g., a computer) owned and/or controlled by the given entity is actually performing the action.

Analysis-ready variables (ARVs) are described that represent perspectives and vehicles by which data are analyzed. ARVs may be used in investigating errors or inconsistencies in data. ARVs may be used to gain insight into data. Further, ARVs may be used in applying an analysis method. ARVs may comprise independent variables, dependent variables, features, outcomes, coordinates, occurrences, non-occurrences and the like and combinations thereof. ARVs may comprise a single variable or a plurality of variables. ARVs may comprise characters, symbols, numbers and the like and combinations thereof. ARVs may be associated with information. For example, ARVs may be associated with cohort selection, treatment comparisons, pharmacovigilance and the like and combinations thereof. ARVs may be associated with code. ARVs may comprise time-interdependent analysis variables (TIAVs).

TIAVs are described that may represent variables associated with time and/or other temporal information. Temporal information may comprise information associated with time, such a day of the week or a calendar month. Temporal information may comprise units of time such as seconds, minutes, hours, days etc. . . . . Temporal information may comprise a difference in time between a first occurrence or non-occurrence of an event and a subsequent occurrence or non-occurrence of the event. Temporal information may comprise time-stamped information. For example, temporal information may comprise time-stamped data. TIAVs may be associated with EHRs and/or patient medical history. TIAVs may be associated with a time of day, a date, a month, a year, and divisions thereof (e.g. hours, minutes, seconds) or other temporal scale and the like and combinations thereof. TIAVs may be associated with units such as seconds, minutes, hours, days, months, years and the like and combinations thereof. TIAVs may be ordinal in scale. For example, TIAVs may be derived from a time-based scale. As a further example, TIAVs may represent a second occurrence or non-occurrence of an event (e.g., a procedure, diagnosis, prescription, therapy, or clinical setting). Further, TIAVs may be associated with periods of time, such as a difference in time between a first occurrence or non-occurrence of an event and subsequent occurrence or non-occurrence of an event. TIAVs may be determined from known information, for instance domain knowledge, or calculated, for instance by an algorithm. TIAVs may comprise information related to patterns such as medication exposure or comorbidity trends. TIAVs may comprise independent variables, dependent variables, features, outcomes, coordinates, occurrences, non-occurrences and the like and combinations thereof. TIAVs may comprise a single variable or a plurality of variables. TIAVs may comprise characters, symbols, numbers and the like and combinations thereof. TIAVs may be associated with a code.

Intermediate data objects are described that bridge source data to ARVs. The intermediate data objects may be in the form of a text string (e.g., a string object), but other forms are specifically contemplated. The intermediate data object may comprise an intermediate data structure. The intermediate data object may comprise a symbolic data structure. These intermediate data objects enable multiple researchers to quickly create specific ARVs most suited for their individual studies. One or more ARVs may be derived from one or more segments (e.g., or a complete) of one or more intermediate data objects. Because the intermediate data objects facilitate rapid creation of analysis variables, the intermediate data objects enable on-the-fly evaluation of patterns and potential issues with the source data. The rapid creation of ARVs may be facilitated by code which derives ARVs from sequences. This makes the creation of ARVs more amenable to automation. SQL or other programming languages may be used to create ARVs from time-stamped EHRs. While the intermediate data objects distill and capture the key information, the intermediate data objects only take up a fraction of the size of the source data.

The intermediate data objects described reduce duplication of data preparation efforts among researchers. Once generated, common text functions may be implemented to locate and count the length of a whole or a segment of an intermediate data object, find or remove text symbols, create a composite intermediate data objects from multiple intermediate data objects, and the like. Additionally, software tools capable of complex pattern matching, such as those based on PERL regular expression, may be used to analyze the intermediate data objects.

FIG. 1 shows a method 100 for generating an intermediate data structure. The method 100 may comprise determining data values of a sequence of events (e.g., a time series) stored in one or more databases at 110. The sequence of events may or in a regular fashion or in an irregular fashion. The sequence of events can comprise a series of values indicative of one or more occurrences or non-occurrences of an event obtained at successive times. The sequence of events may comprise a series of time-stamped events. The sequence of events may be associated with a series of time-stamped records. The sequence of events can comprise any values received (e.g., determined, measured, sampled) over a period of time. The sequence of events may have attributes such as one or more of a unit, a reference point, an information type and an information representation. The reference point may comprise a position of an event in the sequence of events. The reference point may indicate a start date or an end date. The reference point may comprise a censoring point that indicates no record. The reference point may comprise a location of an event where the unit of the event is known. The location of an event within the sequence may be determined based on a time unit. The location of an event may be translated to a time unit by a translation mechanism. The translation mechanism may be simple or complex. The translation mechanism may correlate positions in the sequence with information such as temporal information, for instance a calendar date. The translation mechanism may coalesce events or temporal information and the like and combinations thereof. The information may be determined directly or inferred from EHRs. For example, an international classification of diseases (ICD) code may be determined directly. For example, medication exposure may be inferred as it is derived from a medication release date and days of supply provided, such information being included in an EHR.

The event can comprise a change in state of a person or circumstance. The event may comprise state-based data. The event can be a binary event. For example, the event can be a presence or an absence of a condition (e.g., health condition). By way of example, the values can comprise an indication of whether a patient took a medication (e.g., on a given day, series of days, and the like). The event can be a non-binary event. For example, the event can be a blood pressure or other metric. Other units of time may be used, for example, seconds, minutes, hours, weeks, months, years. The unit of time may be adjusted to account for what is being measured.

The method 100 can comprise generating an intermediate data structure associated with the event at 120. The intermediate data structure may comprise any type of data structure. The intermediate data structure may comprise a string.

The method 100 can comprise determining that each data value of the sequence of events indicates an occurrence of the event or a non-occurrence of the event at 130. For example, the sequence of events can represent medication taken by a patient over time. The values can represent whether the patient took the medication on each day over time. The value can be a code. The value can be extracted from an electronic medical record. The electronic medical record may comprise an EHR. In an embodiment, the intermediate data object may be generated to represent individual patient's histories of medication use, comorbidity diagnosis, and/or clinical setting (inpatient or outpatient) in which a diagnosis was made. The intermediate data object can succinctly capture a longitudinal pattern of the patient's healthcare utilization and clinical information.

The method 100 can comprise representing, in the intermediate data structure, data values of the sequence of events that indicate the occurrence of the event with a first symbol at 140. The first symbol can be any alphanumeric symbol. For example, the first symbol can comprise a "1". By way of example, for a day the patient took the medication, a "1" can be added to the intermediate data structure. The first symbol can comprise a plurality of symbols. By way of example, for a day the patient may be diagnosed with influenza with respiratory manifestations the associated ICD-9-CM code 487.1 may be entered into an electronic medical record for the patient. The first symbol used to represent the presence of the event may be a plurality of symbols (e.g., 4871) indicating the ICD-9 code.

The method 100 can comprise representing, in the intermediate data structure, data values of the sequence of events that indicate the non-occurrence of the event with a second symbol at 150. The second symbol can be any alphanumeric symbol. For example, the first symbol can comprise a "0". By way of example, for a day the patient did not take the medication, a "0" can be added to the intermediate data structure. The second symbol can comprise a plurality of symbols. By way of example, for a day the patient was identified as no longer having influenza with respiratory manifestations, the second symbol used to represent the presence of the event may be a plurality of symbols (e.g., 0000) indicating the absence of the flu.

The intermediate data structure can maintain an order of the first symbols and the second symbols based on the successive times of the sequence of events. For example, for each day the patient took the medication, a "1" is added to the intermediate data structure and for each day the patient did not take the medication, a "0" is added to the intermediate data structure. The 1's and 0's may be added to the intermediate data structure in chronological order (e.g., indicated by the sequence of events). For example, for a patient that took medication on day 1, day 3, and day 5 of a 7 day period, the intermediate data structure may be "1010100". In the event the first symbol and the second symbol comprise a plurality of symbols, the chronological order may be maintained by assigning a number of symbols (e.g., a segment of the intermediate data object) as being indicative of a single occurrence or non-occurrence of the event. For example, every 6 symbols may be associated with an occurrence or non-occurrence of the event. In another example, the 1's and 0's may represent a day a patient was in possession of or not in possession of a medication. In another example, the 1's and 0's may merely represent a day during which there was or was not a prescription for a medication.

In an embodiment, a segment symbol may be inserted after the first symbol or before the second symbol. The segment symbol may indicate a boundary between other symbols. The segment symbol may be any alphanumeric or other symbol. For example, the segment symbol may be a "|". Use of the segment symbol enables the first symbol to be a different length from the second symbol. When searching for specific occurrences or non-occurrences of the event, the segments can be identified using the segment symbol.

A segment identifier can be generated and associated with a segment. The segment identifier can, in one embodiment, be a date or a range of dates or other temporal information. The segment identifier can be a code. The segment identifier(s) can be used to align multiple intermediate data objects. The segment identifiers(s) can be used to extract symbols from a plurality of intermediate data objects from the same segment (e.g., position in the intermediate data objects). In effect, the segment identifier can serve as a key associated to the symbols of the associated segment.

Generating the intermediate data structure associated with the event may comprise generating a plurality of intermediate data structures, wherein each of the plurality of intermediate data structures is associated with a respective event.

The method 100 may comprise receiving a query, wherein the query comprises a time parameter and an event parameter, determining, based on the event parameter, that the query is related to the intermediate data structure (or a plurality of intermediate data structures), and determining, based on the time parameter, one or more first symbols or second symbols in the intermediate data structure (or in the plurality of intermediate data structures). A plurality of intermediate data structures may be identified as related to the event. The time parameter may comprise a time range that comprises a start time or date and an end time or date. The time parameter may comprise a segment identifier and/or a segment range. Determining, based on the time parameter, one or more first symbols or second symbols in the intermediate data structure may comprise determining a position in the intermediate data structure corresponding to the start time or date, determining a position in the intermediate data structure (or in the plurality of intermediate data structures) corresponding to the end time or date, and extracting one or more first symbols or second symbols from the intermediate data structure (or from the plurality of intermediate data structures) located between and including the position in the intermediate data structure corresponding to the start time or date and the position in the intermediate data structure corresponding to the end time or date. The method 100 can comprise extracting data from the one or more databases corresponding to the extracted symbols. The extracted data can comprise analysis-ready variables (ARVs). The extracted symbols can comprise analysis-ready variables (ARVs). The extracted symbols may be combined with extracted symbols resulting from other queries on other intermediate data structures.

Figure 2:
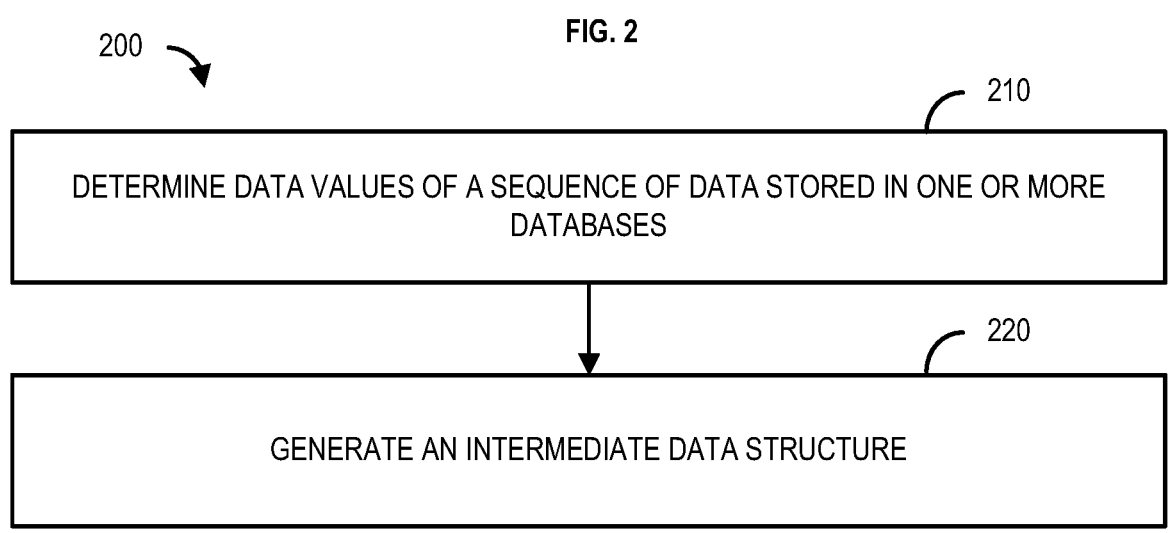
FIG. 2 shows an example method.

FIG. 2 shows a method 200 for generating an intermediate data structure. The method 200 may comprise determining data values of a sequence of events stored in one or more databases at 210. The sequence of events may comprise a series of values indicative of one or more occurrences or non-occurrences of an event obtained at successive times. The sequence of events may have attributes such as one or more of a unit, a reference point, an information type and an information representation. The reference point may comprise a position of an event in the sequence of events. The reference point may indicate a start date or an end date. The reference point may comprise a censoring point that indicates no record. The reference point may comprise a location of an event where the unit of the event is known. The location of an event within the sequence may be determined based on a time unit. The location of an event may be translated to a time unit by a translation mechanism. The translation mechanism may be simple or complex. The translation mechanism may correlate positions in the sequence with information such as temporal information, for instance a calendar date. The translation mechanism may coalesce events or temporal information and the like and combinations thereof. The information may be determined directly or inferred from EHRs. For example, an international classification of diseases (ICD) code may be determined directly. For example, medication exposure may be inferred as it is derived from a medication release date and days of supply provided, such information being included in an EHR.

The method 200 may comprise generating an intermediate data structure at 220. The intermediate data structure may comprise a string of symbols. The string of symbols may comprise one or more symbols. Each symbol may be indicative of an occurrence of the event or a non-occurrence of the event. The string of symbols may maintain an order of the first symbols and the second symbols based on the successive times of the sequence of events.

In an embodiment, a segment symbol may be inserted after the first symbol or before the second symbol. The segment symbol may indicate a boundary between other symbols. The segment symbol may be any alphanumeric or other symbol. For example, the segment symbol may be a "|". Use of the segment symbol enables the first symbol to be a different length from the second symbol. When searching for specific occurrences or non-occurrences of the event, the segments can be identified using the segment symbol.

A segment identifier can be generated and associated with a segment. The segment identifier can, in one embodiment, be a date or a range of dates or other temporal information. The segment identifier can be a code. The segment identifier(s) can be used to align multiple intermediate data objects. The segment identifiers(s) can be used to extract symbols from a plurality of intermediate data objects from the same segment (e.g., position in the intermediate data objects). In effect, the segment identifier can serve as a key associated to the symbols of the associated segment.

Generating the intermediate data structure may comprise generating a plurality of intermediate data structures, wherein each of the plurality of intermediate data structures is associated with a respective event.

The method 200 may comprise receiving a query, wherein the query comprises a time parameter and an event parameter, determining, based on the event parameter, that the query is related to the intermediate data structure (or to a plurality of intermediate data structures), and determining, based on the time parameter, one or more first symbols or second symbols in the intermediate data structure (or in the plurality of intermediate data structures). A plurality of intermediate data structures may be identified as related to the event. The time parameter may comprise a time range that comprises a start time or date and an end time or date. The time parameter may comprise a segment identifier and/or a segment range. Determining, based on the time parameter, one or more first symbols or second symbols in the intermediate data structure may comprise determining a position in the intermediate data structure (or in the plurality of intermediate data structures) corresponding to the start time or date, determining a position in the intermediate data structure corresponding to the end time or date, and extracting one or more first symbols or second symbols from the intermediate data structure (or from the plurality of intermediate data structures) located between and including the position in the intermediate data structure corresponding to the start time or date and the position in the intermediate data structure corresponding to the end time or date. The method 200 can comprise extracting data from the one or more databases corresponding to the extracted symbols. The extracted data can comprise analysis-ready variables (ARVs). The extracted symbols can comprise analysis-ready variables (ARVs). The extracted symbols may be combined with extracted symbols resulting from other queries on other intermediate data structures.

Figure 3:
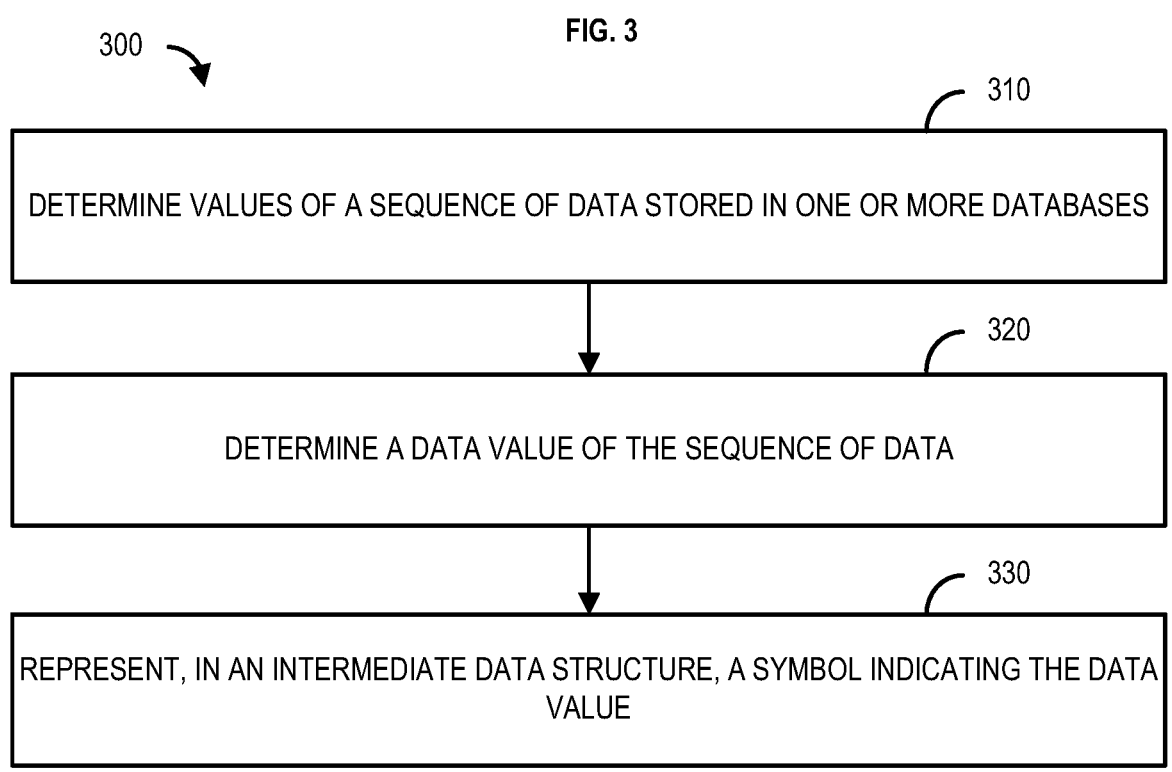
FIG. 3 shows an example method.

FIG. 3 shows a method 300 for generating an intermediate data structure. The method 300 may comprise determining values of a sequence of data (e.g., a time series) stored in one or more databases at 310. The sequence of data can comprise a series of values indicative of one or metrics, readings, measurements, and the like obtained at successive times. For example, the sequence of data can comprise a sequence of blood pressure readings for a patient over time. The sequence of data can comprise any values received (e.g., determined, measured, sampled) over a period of time. The sequence of data can comprise a series of values indicative of one or more occurrences or non-occurrences of an event obtained at successive times. The event can comprise a change in state of a person or circumstance. For example, the event can be a presence or an absence of a condition (e.g., health condition). By way of example, the values can comprise an indication of whether a patient took a medication (e.g., on a given day, series of days, and the like). Other units of time may be used, for example, seconds, minutes, hours, weeks, months, years. The unit of time may be adjusted to account for what is being measured. The sequence of data may have attributes such as one or more of a unit, a reference point, an information type and an information representation. The reference point may comprise a position of an event in the sequence of events. The reference point may indicate a start date or an end date. The reference point may comprise a censoring point that indicates no record. The reference point may comprise a location of data where the unit of the data is known. The location of data within the sequence may be determined based on a time unit. The location of the data may be translated to a time unit by a translation mechanism. The translation mechanism may be simple or complex. The translation mechanism may correlate positions in the sequence with information such as temporal information, for instance a calendar date. The translation mechanism may coalesce data or temporal information and the like and combinations thereof. The information may be determined directly or inferred from EHRs. For example, an international classification of diseases (ICD) code may be determined directly. For example, medication exposure may be inferred as it is derived from a medication release date and days of supply provided, such information being included in an EHR.

The method 300 can comprise determining each (or at least one) data value of the sequence of data at 320. The data value can be a code, a metric, a reading, a measurement, and the like. The data value can comprise a one or a plurality of alphanumeric characters. The data value can be extracted from an electronic medical record. For example, the sequence of data can represent medication taken by a patient over time. The data values can represent whether the patient took the medication on each day over time. In an embodiment, the intermediate data object may be generated to represent individual patient's histories of medication use, comorbidity diagnosis, and/or clinical setting (inpatient or outpatient) in which a diagnosis was made.

The method 300 can comprise representing, in an intermediate data structure, a symbol indicating the alphanumeric characters of the data value at 330. The intermediate data structure may comprise any type of data structure. The intermediate data structure may comprise a string, an array, and the like. The symbol can be any alphanumeric symbol. For example, the symbol can comprise a "1". By way of example, for a day the patient may be diagnosed with influenza with respiratory manifestations the associated ICD-9-CM code 487.1 may be entered into an electronic medical record for the patient. The symbol used to represent the presence of the condition may be a plurality of symbols (e.g., 4871) indicating the ICD-9 code. The alphanumeric data value of "4871" would be entered into the intermediate data object as a first symbol of "4," a second symbol of "8," a third symbol of "7," and a fourth symbol of "1." The symbols would be inserted at the same segment) of the intermediate data object. A segment of the intermediate object represents a point in time associated with the corresponding data value.

The intermediate data structure can maintain an order of the symbols based on the successive times of the sequence of data. For example, for each day the patient took the medication, a "1" is added to the intermediate data structure and for each day the patient did not take the medication, a "0" is added to the intermediate data structure. The 1's and 0's may be added to the intermediate data structure in chronological order (e.g., indicated by the sequence of events). For a patient that took medication on day 1, day 3, and day 5 of a 7 day period, the intermediate data structure may be "1010100". In the event the symbol comprises a plurality of symbols, the chronological order may be maintained by assigning a number of symbols as a segment. For example, every 6 symbols may be associated with a segment of the intermediate data structure.

In an embodiment, a segment symbol may be inserted between symbols. The segment symbol may indicate a boundary between other symbols. The segment symbol may be any alphanumeric or other symbol. For example, the segment symbol may be a "|". Use of the segment symbol enables the symbols to be of different length. When searching for specific conditions, the segments can be identified using the segment symbol.

A segment identifier can be generated and associated with a segment. The segment identifier can, in one embodiment, be a date or a range of dates or other temporal information. The segment identifier can be a code. The segment identifier(s) can be used to align multiple intermediate data objects. The segment identifiers(s) can be used to extract symbols from a plurality of intermediate data objects from the same segment (e.g., position in the intermediate data objects). In effect, the segment identifier can serve as a key associated to the symbols of the associated segment.

Generating the intermediate data structure associated with the event may comprise generating a plurality of intermediate data structures, wherein each of the plurality of intermediate data structures is associated with a condition.

The method 300 may comprise receiving a query, wherein the query comprises a time parameter and a condition parameter, determining, based on the condition parameter, that the query is related to the intermediate data structure (or to a plurality of intermediate data structures), and determining, based on the time parameter, one or more symbols in the intermediate data structure (or in the plurality of intermediate data structures). A plurality of intermediate data structures may be identified as related to the condition. The time parameter may comprise a time range that comprises a start time or date and/or an end time or date. The time parameter may comprise a segment identifier and/or a segment range. Determining, based on the time parameter, one or more symbols in the intermediate data structure may comprise determining a position in the intermediate data structure (or in the plurality of intermediate data structures) corresponding to the start time or date, determining a position in the intermediate data structure corresponding to the end time or date, and extracting one or more symbols from the intermediate data structure (or from the plurality of intermediate data structures) located between and including the position in the intermediate data structure corresponding to the start time or date and the position in the intermediate data structure corresponding to the end time or date. The method 300 can comprise extracting data from the one or more databases corresponding to the extracted symbols. The extracted data can comprise analysis-ready variables (ARVs). The extracted symbols can comprise analysis-ready variables (ARVs). The extracted symbols may be combined with extracted symbols resulting from other queries on other intermediate data structures.

Figure 4:
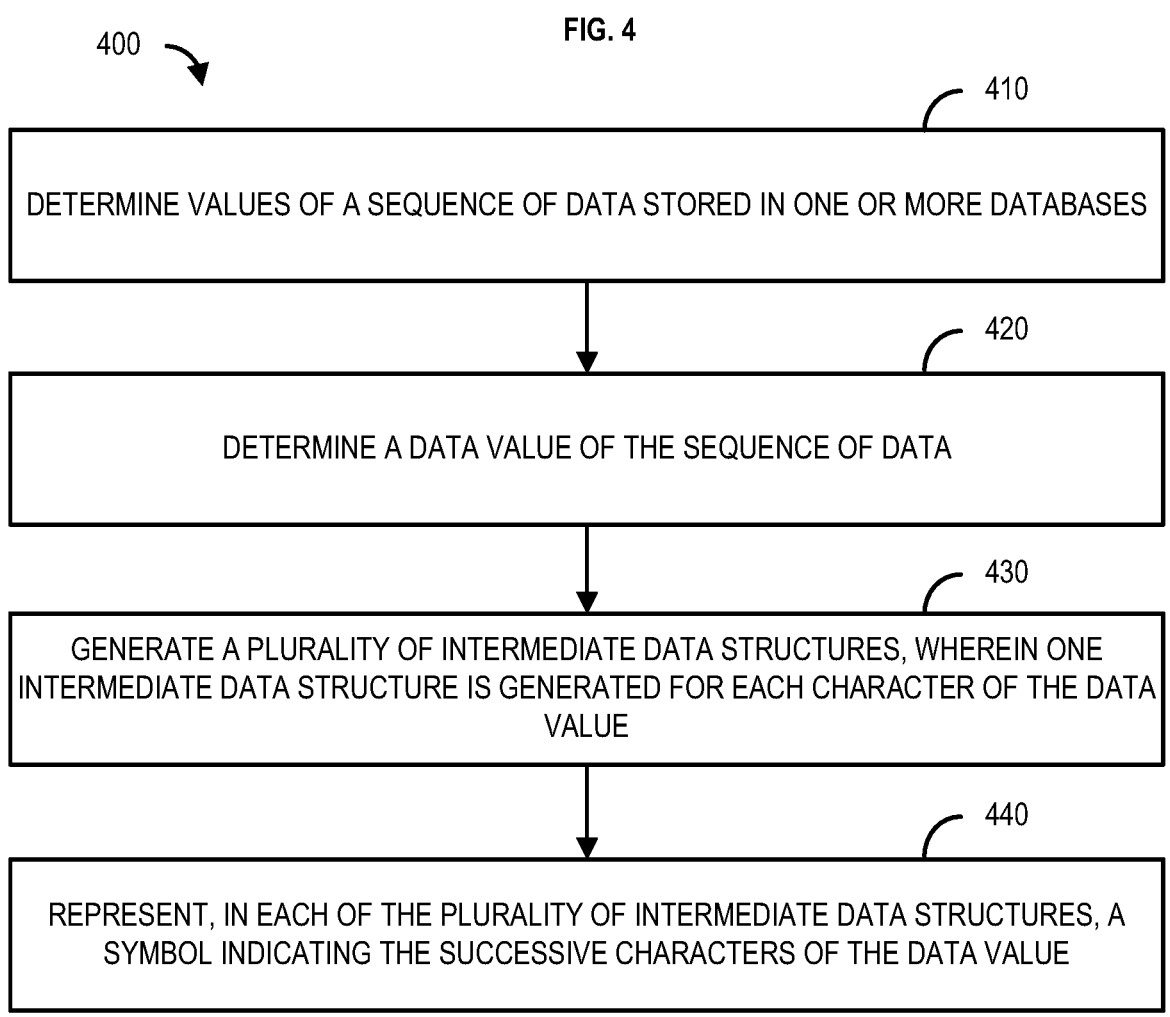
FIG. 4 shows an example method.

FIG. 4 shows a method 400 for generating a plurality of intermediate data structures. The method 400 may comprise determining values of a sequence of data (e.g., a time series) stored in one or more databases at 410. The sequence of data can comprise a series of values indicative of one or more metrics, readings, measurements, and the like obtained at successive times. For example, the sequence of data can comprise a sequence of blood pressure readings for a patient over time. The sequence of data can comprise any values received (e.g., determined, measured, sampled) over a period of time. The sequence of data can comprise a series of values indicative of one or more occurrences or non-occurrences of an event obtained at successive times. The event can comprise a change in state of a person or circumstance. For example, the event can be a presence or an absence of a condition (e.g., health condition). By way of example, the values can comprise an indication of whether a patient took a medication (e.g., on a given day, series of days, and the like). Other units of time may be used, for example, seconds, minutes, hours, weeks, months, years. The unit of time may be adjusted to account for what is being measured. The sequence of data may have attributes such as one or more of a unit, a reference point, an information type and an information representation. The reference point may comprise a position of data in the sequence of data. The reference point may indicate a start date or an end date. The reference point may comprise a censoring point that indicates no record. The reference point may comprise a location of data where the unit of the data is known. The location of data within the sequence may be determined based on a time unit. The location of data may be translated to a time unit by a translation mechanism. The translation mechanism may be simple or complex. The translation mechanism may correlate positions in the sequence of data with information such as temporal information, for instance a calendar date. The translation mechanism may coalesce data or temporal information and the like and combinations thereof. The information may be determined directly or inferred from EHRs. For example, an international classification of diseases (ICD) code may be determined directly. For example, medication exposure may be inferred as it is derived from a medication release date and days of supply provided, such information being included in an EHR.

The method 400 can comprise determining each (or at least one) data value of the sequence of data at 420. The data value can be a code, a metric, a reading, a measurement, and the like. The data value can comprise a plurality of alphanumeric characters. The data value can be extracted from an electronic medical record. For example, the sequence of data can represent medication taken by a patient over time. The data values can represent whether the patient took the medication on each day over time. In an embodiment, the intermediate data object may be generated to represent individual patient's histories of medication use, comorbidity diagnosis, and/or clinical setting (inpatient or outpatient) in which a diagnosis was made.

The method 400 can comprise generating a plurality of intermediate data structures, wherein one intermediate data structure is generated for each character of the plurality of alphanumeric characters of the data value at 430. The intermediate data structure may comprise any type of data structure. The intermediate data structure may comprise a plurality of strings, an array, and the like.

The method 400 can comprise representing, in each of the plurality of intermediate data structures, a symbol indicating the successive alphanumeric characters of the data value at 440. The symbol can be any alphanumeric symbol. For example, the symbol can comprise a "1". By way of example, for a day the patient may be diagnosed with influenza with respiratory manifestations the associated ICD-9-CM code 487.1 may be entered into an electronic medical record for the patient. The symbol used to represent the presence of the condition may be a plurality of symbols (e.g., 4871) indicating the ICD-9 code. The alphanumeric data value of "4871" would be entered into a first intermediate data object as a symbol of "4," a second intermediate data object as a symbol of "8," a third intermediate data object as a symbol of "7," and a fourth intermediate data object as a symbol of "1." The symbols would be inserted at the same relative position (e.g., segment) in the respective intermediate data objects. For example:

xxxx4xxxx
xxxx8xxxx
xxxx7xxxx
xxxx1xxxx

Accordingly, the plurality of intermediate data objects can be queried for the symbols at the same position and the condition of the patient can be determined for the time associated with the segment.

The plurality of intermediate data structures can maintain an order of the symbols based on the successive times of the sequence of data. In an embodiment, a segment symbol may be inserted after the first symbol or before the second symbol. The segment symbol may indicate a boundary between other symbols. The segment symbol may be any alphanumeric or other symbol. For example, the segment symbol may be a "|". Use of the segment symbol enables the first symbol to be a different length from the second symbol. When searching for specific occurrences or non-occurrences of the condition, the segments can be identified using the segment symbol.

A segment identifier can be generated and associated with a segment. The segment identifier can, in one embodiment, be a date or a range of dates or other temporal information. The segment identifier can be a code. The segment identifier(s) can be used to align multiple intermediate data objects. The segment identifiers(s) can be used to extract symbols from a plurality of intermediate data objects from the same segment (e.g., position in the intermediate data objects). In effect, the segment identifier can serve as a key associated to the symbols of the associated segment.

The method 400 may comprise receiving a query, wherein the query comprises a time parameter and a condition parameter, determining, based on the condition parameter, that the query is related to the plurality of intermediate data structures, and determining, based on the time parameter, one or more symbols in the plurality of intermediate data structures. A plurality of intermediate data structures may be identified as related to the condition. The time parameter may comprise a time range that comprises a start time or date and an end time or date. The time parameter can comprise a start segment and/or an end segment. Determining, based on the time parameter, one or more symbols in the plurality of intermediate data structures may comprise determining a position in the plurality of intermediate data structures corresponding to the start time or date, determining a position in the plurality of intermediate data structures corresponding to the end time or date, and extracting one or more symbols from the plurality of intermediate data structures located between and including the position in the plurality of intermediate data structures corresponding to the start time or date and the position in the plurality of intermediate data structures corresponding to the end time or date. The method 400 can comprise extracting data from the one or more databases corresponding to the extracted symbols. The extracted data can ARVs. The extracted symbols can comprise ARVs. The extracted symbols may be combined with extracted symbols resulting from other queries on other intermediate data structures. In an example, multiple sequences (e.g., string block) may represent an element of a sequence.

Figure 5:
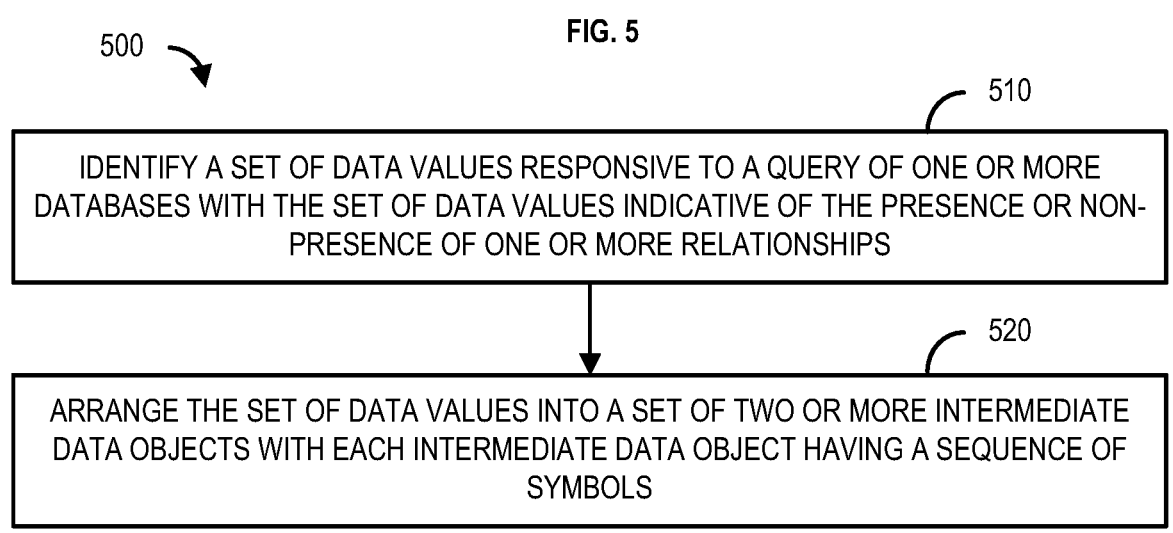
FIG. 5 shows an example method.

FIG. 5 shows a method 500 comprising identifying a set of data values responsive to a query of one or more databases with the set of data values indicative of the presence or non-presence of one or more relationships at 510. The method 500 may comprise arranging the set of data values into a set of two or more intermediate data objects with each intermediate data object having a sequence of symbols at 520. Each of the symbols may have an imputed unique key based upon a position of the symbol within its associated intermediate data object wherein each intermediate data object shares the imputed unique keys for related positions of the symbols in each particular intermediate data object.

The one or more relationships may include an occurrence or non-occurrence of an event at pre-identified periods and wherein each imputed unique key represents one of the pre-identified periods. Each intermediate data object may include a text string and wherein each symbol includes a text character. Each intermediate data object may include a data array and wherein each symbol includes a predetermined number N characters with N>1. The one or more relationships may include a classification of codes having a relative positional order and wherein each imputed unique key represents one of the relative positional orders.

Figure 6:
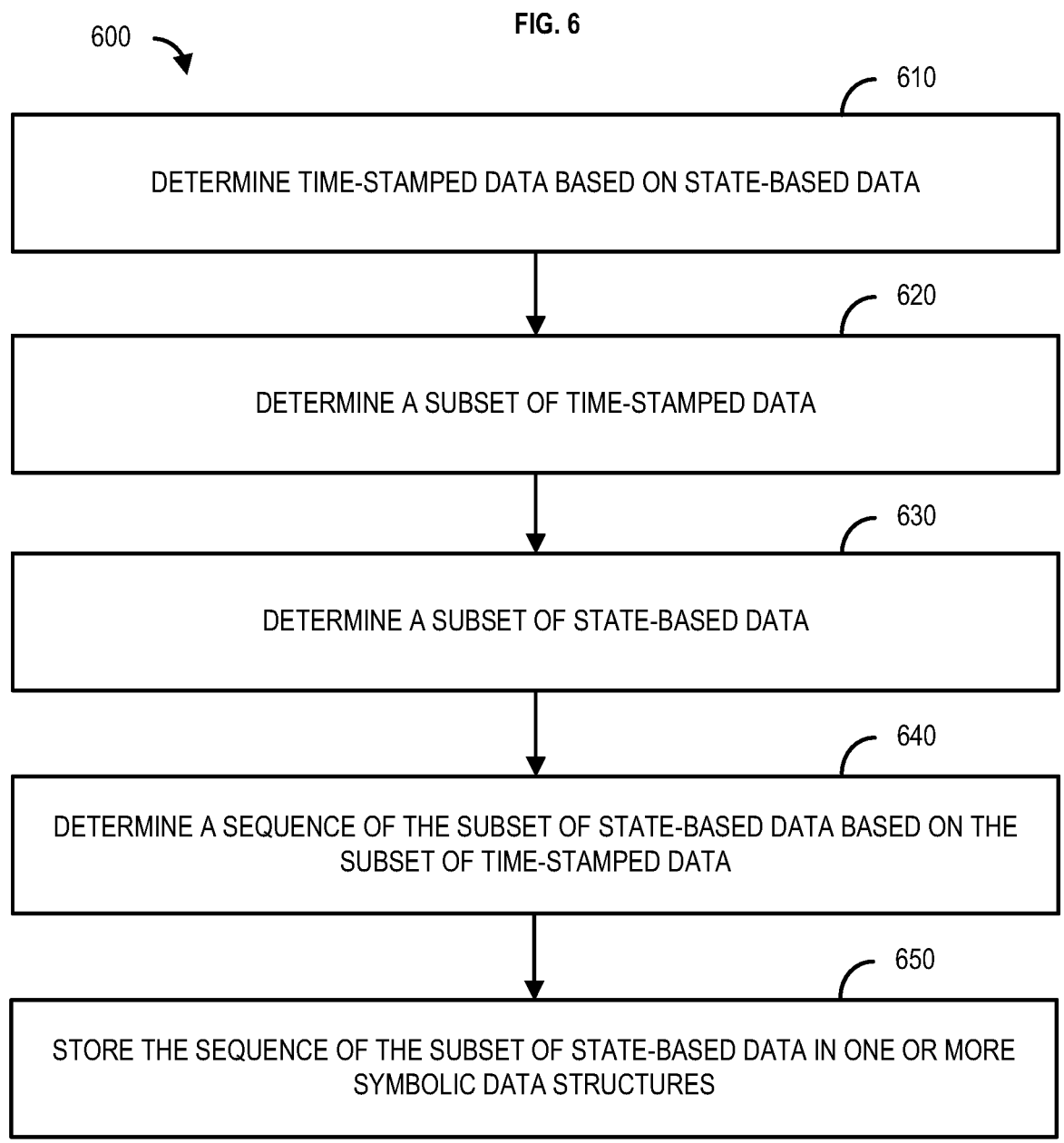
FIG. 6 shows an example method.

FIG. 6 shows a method 600 comprising determining a set of time-stamped data at 610. The time-stamped data may be based on state-based data. State-based data may comprise medical conditions associated with one or more persons. State-based data may be determined by querying a database. State-based data may comprise medical treatments associated with one or more persons. State-based data may comprise medical diagnoses associated with one or more persons. The time-stamped data may comprise temporal information associated with state-based data. For example, the time at which someone checked into a clinic or the date of an incident. Information related to time-stamped data may be retrieved from an intermediate data object. Information related to time-stamped data may be retrieved from a symbolic data structure or the like. The time-stamped data may comprise an EHR. The EHR may be stored in a database. The database may comprise a plurality of tables. The time-stamped data may be associated with an event or a sequence of events. The time-stamped data may be associated with a state or a change of state of a person or circumstance. For example, the time-stamped data may indicate a given day (e.g., a day of week, a specific day in a year, etc.) or series of days (e.g., a week, a succession of days, etc.) and the like. The time-stamped data may be associated with state-based data. State-based data may comprise an event or sequence of events. The state-based data may be associated with a state or a change of state of a person or circumstance. For example, state-based data may be indicative of a diagnosis or therapy or the like or combinations thereof. The time-stamped data may be determined by querying a database.

At step 620, a subset of time-stamped data may be determined. The subset of time-stamped data may be determined by analyzing the time-stamped data. The subset of time-stamped data may be determined according to whether or not the time-stamped data satisfies a criteria or set of criteria. The subset of the time-stamped data may comprise all, or a portion of the time-stamped data. The subset of the time-stamped data may be a representation of the time-stamped data.

At step 630, a subset of state-based data may be determined. The subset of state-based data may be determined according to whether or not the state-based data satisfies a criteria or set of criteria. The subset of the state-based data may comprise all, or a portion of the state-based data. The subset of the state-based data may be a representation of the state-based data.

At step 640, a sequence of the subset of state-based data may be determined. The sequence of the subset of state-based data may be determined based on the subset of the state-based data. The sequence of the subset of state-based data may be determined based on the subset of time-stamped data. The sequence may be determined based on temporal information, diagnostic information, demographic information, or any other way. By way of example, the sequence may be ordered according to temporal information like a calendar date. The sequence may comprise an arrangement of the state-based data.

At step 650, the sequence of the subset of state-based data may be stored in one or more symbolic structures. A symbolic structure may comprise a data object or structure. For example, a symbolic structure may comprise an intermediate data object or intermediate data structure. The symbolic data structure may comprise state-based data. The state-based data may be associated with a particular member of a population. Storing the subset of state-based data may comprise converting time-stamped data to state-based data.

The method may comprise a processor-implemented method for a conversion of a set of time-stamped data derived from a set of state-based parameters of a system, the set of time-stamped data distributed in a plurality of tables of a database supported on a stored program processing system including a set of instructions executable on a processor of the stored program processing system to implement the method comprising: querying the set of time-stamped data from the database producing a subset of the set of time-stamped data, analyzing the subset of the time-stamped data producing a subset of the set of state-based parameters, and sequencing the subset of the set of state-based parameters in a set of symbolic data structures while preserving the subset of the set of state-based parameters within the symbolic data structure.

The method may be executed wherein the system includes one or more electronic health records of a population, wherein the set of state-based parameters include one or more medical data selected from the group consisting of medical conditions of the population, medical treatments of the population, medical diagnoses of the population, and combinations thereof, wherein the set of time-stamped data includes one or more temporal snapshots of one or more of the set of state-based parameters for particular members of the population.

The method may be executed wherein the set of symbolic data structures includes one or more sequences of computer-readable symbols, each sequence of computer-readable symbols associated with a specific particular member of the population, each of the sequences mapping at least a portion of the state-based parameters for the specific particular member of the population.

By way of example, and not limitation, provided are applications of the disclosed methods using data from Veteran Administration's research databases, Corporate Data Warehouse (CDW) for 1,452,098 veterans who had received a PTSD diagnosis between 2007 and 2015.

In the first example, strings of '0's and '1's were used to represent each patient's history of PTSD medication use. In the second example, strings of numbers and letters represent diagnosis and clinical setting in which the diagnosis was made. Each position of the string corresponds to one day. Calendar date of each position can be determined from the calendar date of the first position, which was the start date. Start date was inferred for each patient and shared by all the strings for the same patient.

An application of the methods may comprise a symbolic representation of PTSD medication use. For example, in a paired study to compare 4 classes (Antipsychotics, Tricyclic antidepressants, Mirtazapine, Prazosin) of PTSD augmenting medication, a query was formulated to select patients who can serve as their own controls. Specifically, the qualifying patient should have a 2-year period around an index date of an augmenting medication such that the patient 1) was free of the index augmenting medication $\geq X$ days during the pre-index year, 2) was on the index augmenting medication $\geq X$ days during the post-index year, 3) was on a serotonin reuptake inhibitor (SRI) $\geq X$ days during the pre and post index year. In addition, it was considered whether the required minimum days on the medication should be over the entire year or a shorter period (30, 60, 120 days), and whether days on both augmenting medication and SRI should exceed a set minimum.

Text strings of '0's and '1's were created for each patient. Each text string represents the history of an augmenting or SRI medication use within the study period, from Jan. 1, 2007 through Dec. 31, 2015. All strings for the same patient have the same length, with each position representing 1 day. The first position corresponds to the start date. Start date is the later of 1) beginning of the study period, and 2) when the patient's pharmacy information first became available. In other words, start date was the earliest date that information of a filled prescription was expected to be in the data. For example, if the patient's medication record started before the study period, his start date would be Jan. 1, 2007. However, if the patient's medication records started on Jun. 15, 2014, his start date would be Jun. 15, 2014. All strings end on Dec. 31, 2015.

Figure 7:
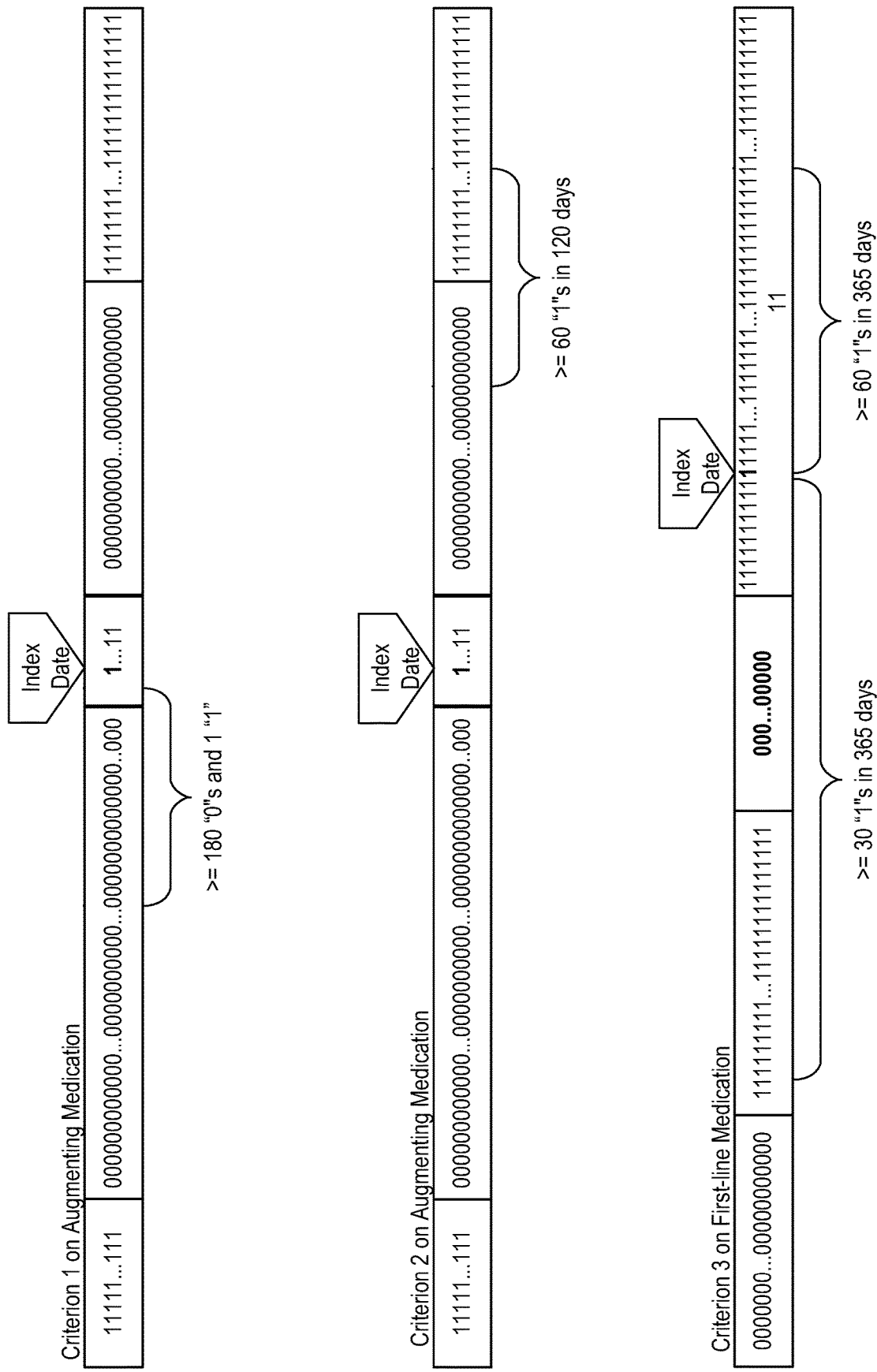
FIG. 7 shows an example of a medication string satisfying certain criteria.

Prescription information was translated into a series of '0's and '1's by their release dates and days' supply and allow 'stashing'. For example, 2 30-day prescriptions released on Jul. 30, 2010 and Aug. 25, 2010 were represented by 60 '1's from Jul. 30, 2010 through Sep. 27, 2010. The binary digit indicated whether the patient was on the medication that day (1=YES, 0=NO). To assess degrees of medication overlap, composite binary strings were created from the 2 individual medication strings by comparing characters at the same position. If characters were both '1', then the corresponding position of the composite string is '1' (overlap); otherwise it's '0' (no overlap). An example of a medication string meeting satisfying certain criteria is shown in FIG. 7. Criteria may be associated with temporal information, prescription information, or other relevant information.

Figure 8A:
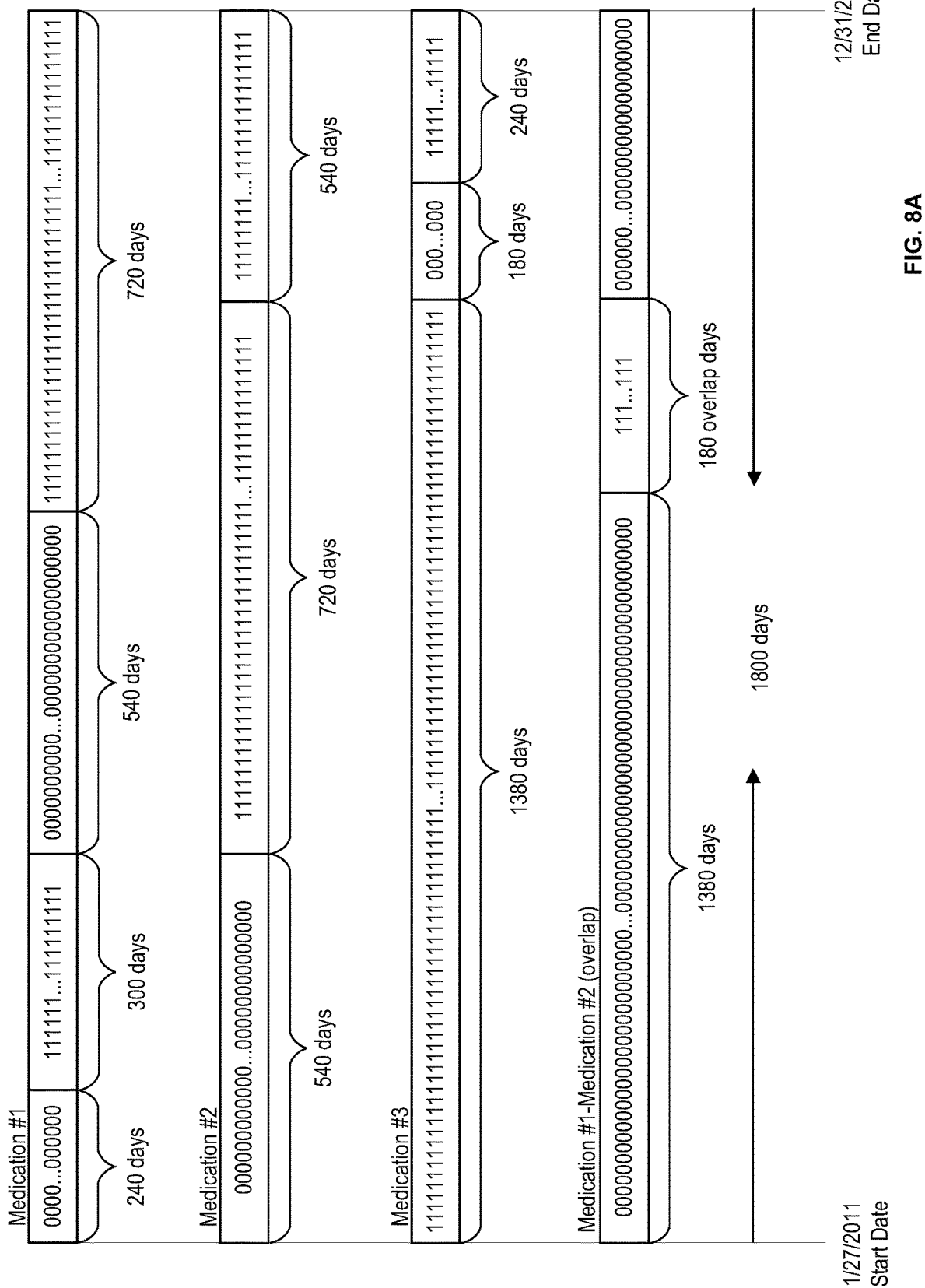
FIG. 8A shows an example of text strings of a hypothetical patient.
Figure 8B:
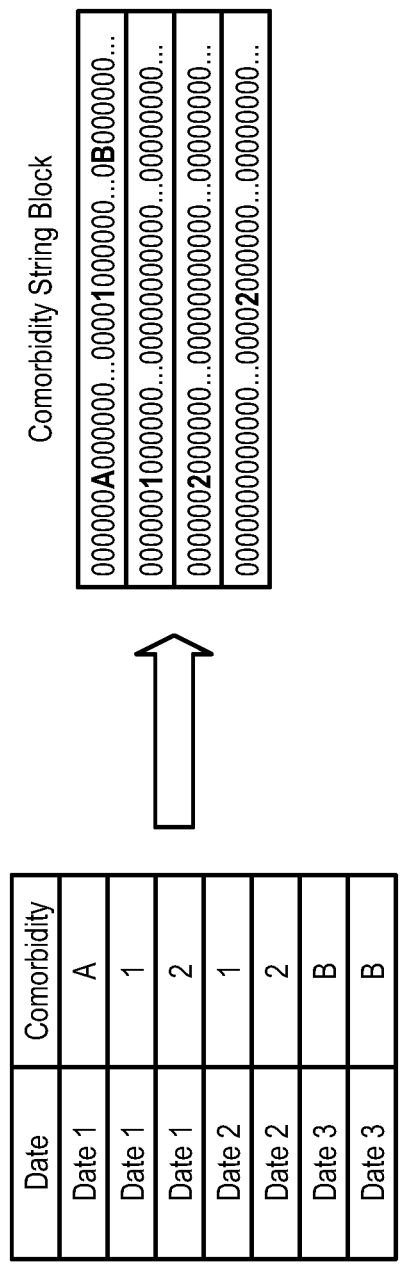
FIG. 8B shows an example string block.

Some patients' augmenting regimens overlapped, making it difficult to attribute the effect to a single regimen. The degree of overlap was quantified by the number of days the patient was on an augmenting medication of a class different than the index medication during the 2-year window. For a hypothetical patient whose index medication was Antipsychotics (AAP) and was also on Prazosin (PRA) during the 2-year qualifying period. From composite strings of AAP-PRA, days of overlapping could be determined. One could create both fixed and time-varying variables to quantify the degrees of overlapping. Total days of overlap over 2 years is a fixed covariate; proportion of overlapping days in the 30 days immediately before the dates of the outcome measurements is a time-varying covariate. The first step of creating a time-varying covariate may be to translate measurement dates into position numbers in the string. Those positions 'stake' the search segments. For example, the substring on and immediately before an outcome measurement date is the segment of length 30, which ends on the position corresponding to the measurement date. FIG. 8A depicts example text strings of a hypothetical patient. FIG. 8B shows an example string block.

An application of the methods may comprise symbolic representation of comorbidity and inpatient/outpatient setting of diagnosis. For example, for each patient 2 strings were created to represent comorbidity and diagnosis setting. Numbers 1 to 9 and letters A to H were used to represent the 17 comorbidities in Quan's Enhanced Charlson Comorbidity Index based on ICD9 codes (Table 1). Letters 'I' and 'O' represent inpatient and outpatient respectively. Since the VA officially transitioned from ICD9 to ICD10 on Oct. 1, 2015, the study period was restricted to Jan. 1, 2007 through Sep. 30, 2015. The start date was the earlier of the earliest diagnosis date and Jan. 1, 2007.

TABLE 1

| Symbol | Comorbidity |
| --- | --- |
| 1 | Myocardial infarction |
| 2 | Congestive heart failure |
| 3 | Peripheral vascular disease |
| 4 | Cerebrovascular disease |
| 5 | Dementia |
| 6 | Chronic pulmonary disease |
| 7 | Rheumatic disease |
| 8 | Peptic ulcer disease |
| 9 | Mild liver disease |
| A | Diabetes without chronic complication |
| B | Diabetes with chronic complication |
| C | Hemiplegia or paraplegia |
| D | Renal disease |
| E | Any malignancy, including lymphoma and leukemia, except malignant neoplasm of skin |
| F | Moderate or severe liver disease |
| G | Metastatic solid tumor |
| H | AIDS/HIV |

Of the 1.4 million patients, 860,826 of them had at least one of the 17 comorbidities. Patients were grouped into separate cohorts by the year of their start date (Table 2).

TABLE 2

| start_yr | Frequency | Percent | Cumulative Frequency |
| --- | --- | --- | --- |
| <2007 | 635577 | 73.83 | 635577 |
| 2007 | 38331 | 4.45 | 673908 |
| 2008 | 36753 | 4.27 | 710661 |
| 2009 | 36894 | 4.29 | 747555 |
| 2010 | 34394 | 4.00 | 781949 |
| 2011 | 27574 | 3.20 | 809523 |
| 2012 | 21139 | 2.46 | 830662 |
| 2013 | 15440 | 1.79 | 846102 |
| 2014 | 10844 | 1.26 | 856946 |
| 2015 | 3880 | 0.45 | 860826 |

For the same patient, strings of comorbidity and clinical setting had the same length, representing start date to Sep. 30, 2015. If a patient received different comorbidities on the same date, the corresponding position on the comorbidity string was represented by the higher comorbidity condition. Similarly, if a patient received diagnoses in both outpatient and inpatient settings, the corresponding position on the clinical setting string was represented as outpatient.

Strings may be used to represent comorbidities diagnosed on different dates. For example, strings may be used to represent comorbidities diagnosed on three different dates. Strings may contain temporal information such as a date or time. Further, strings may comprise information related to comorbidity, medication, treatment, therapies, and other information and combinations thereof. Diagnoses received on the same date may be represented on a separate string. Strings may be based on functions which define sections. Strings may comprise substrings. The functions may be applied to strings or substrings. Sections may represent a measurement period, a code, or other information. An example is show in Table 3.

With these strings, a Charlson Comorbidity Index could be quickly calculated for any subset of patients, using diagnoses information from any measurement period. Total diagnosis dates was used as a proxy measurement for the extent of health service utilization.

Analysis variables may be used to determine patient eligibility (table 3). Analysis variables may comprise information such as position of an index date, information related to medications, treatments, therapies and the like and combinations thereof. Analysis variables may comprise index information such as index medication, or temporal index information such as a start date or end date. Variables may comprise any type of variables for example, numeric, alphabetic, symbolic and the like and combinations thereof. Variable types may comprise dependent and independent variables and the like and combinations thereof. Functions may be used to determine patient eligibility. Functions may comprise simple text functions or complex text functions and the like. For example, a function may comprise a PRXMATCH function, a SUBSTR function, a COMPRESS function, or a LENGTHN function or the like and combinations thereof. An example is shown in Table 3.

TABLE 3

| Time-Depending Analysis Variable | Variable Type | Functions Used |
| --- | --- | --- |
| Position of index date | Numeric | PRXMATCH |
| Days on index medication within window of Z days | Numeric | SUBSTR, COMPRESS, LENGTHN |
| Days on first-line medication during pre-index year | Numeric | SUBSTR, COMPRESS, LENGTHN |
| Days on first-line medication during post-index year | Numeric | SUBSTR, COMPRESS, LENGTHN |
| Days on both first-line and index medications during pre-index year | Numeric | SUBSTR, COMPRESS, LENGTHN |
| Days on both first-line and index medications during post-index year | Numeric | SUBSTR, COMPRESS, LENGTHN |

Applying the methods herein may generate results. For example, regarding the first application described above, the final selection criteria are 1) patient had at least 180 days free of the index augmenting medication prior to the start of the regimen, 2) patient on the index medication ≥60 days in a 120-day period during the post-index year, 3) patient on SRI ≥30 and ≥60 days during the pre and post index year, respectively. SAS function PRXMATCH was used on augmenting medication string to find a series of 180 or more '0's followed by a single '1'. If found, criterion 1 was satisfied and position of the '1' (index date) was noted, and the search advanced. For criterion 2, function SUBSTR was used to define a search window of length 120, starting from the position of the index date. Next, the number of '1's was counted using functions COMPRESS and LENGTHN in the search window. The 120-character search window slid over one position at a time. If the count was ≥60, the search advanced. For the last criterion, first step was to locate the 2 segments of length 365 around the index position on the SRI string using function SUBSTR. Next functions COMPRESS and LENGTHN were used to count the number of '1's in each segment. If the counts were ≥30 and ≥60, respectively, in pre and post segment, the patient met the selection criteria. Each search window was slid over one position at a time and the number of 1's stored in a TIAV. The distributions of these TIAVs were analyzed to determine the best values of variables. Lastly, respective TIAV of days on first-line medication and overlap were similarly determined on the first-line medication and overlap strings. The index date and pre- and post-periods occupy the same positions on the first-line and overlap strings as on the augmenting medication string. This is because the sequences for the same patient start on the same date. This arrangement simplifies the programming, but is not essential to the method. FIG. 9 shows example of a time-varying covariate.

The methods described herein may be applied to longitudinal studies. Longitudinal studies using administration data have a higher risk of confounding by uncontrolled factors. The risk can be assessed by determining a correlation between extraneous factors and responses. However, creating time-varying covariate from source data is more time consuming than fixed covariate, as it depends on the timing of the outcome measurements. Because the intermediate data objects capture the information in a continuous chronological order, the intermediate data objects can be used to determine time-varying covariate values, regardless of the timing of the measurements.

Figure 10:
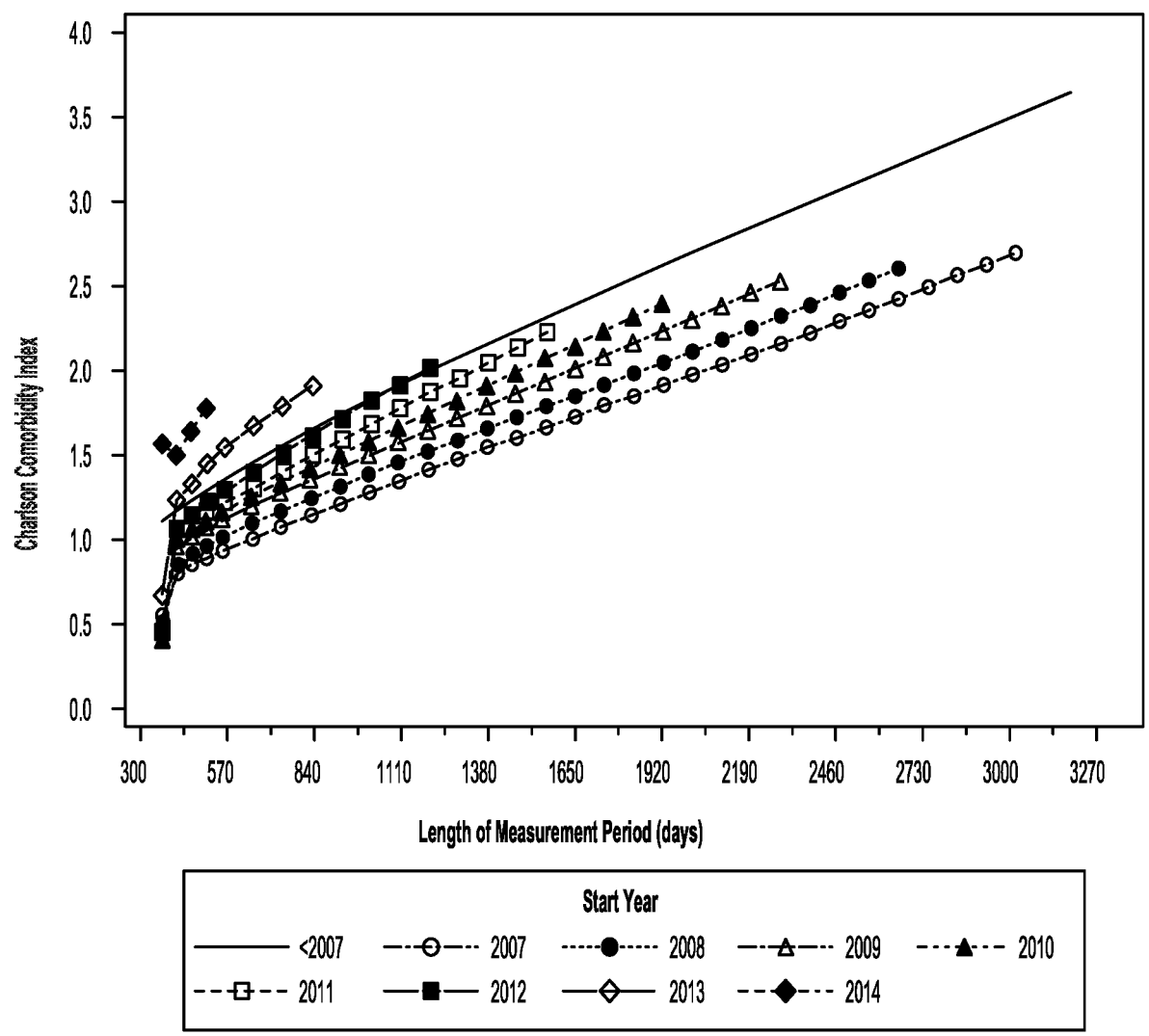
FIG. 10 shows an example Charlson Comorbidity Index (CCI) by length of measurement period.

Applying the methods herein may generate results. For example, regarding the second application described above, The SAS function SUBSTR was used to define the measurement period and function FIND to look for letters and symbols representing each comorbidity. Binary (0=not found, 1=found) variables for each of the comorbidity were created. Charlson Comorbidity Index (CCI) was simply the weighted sum of 17 binary variables. FIG. 10 depicts CCI by length of measurement period, from 365 to 3195 days, at 90-day increments.

Figure 11:
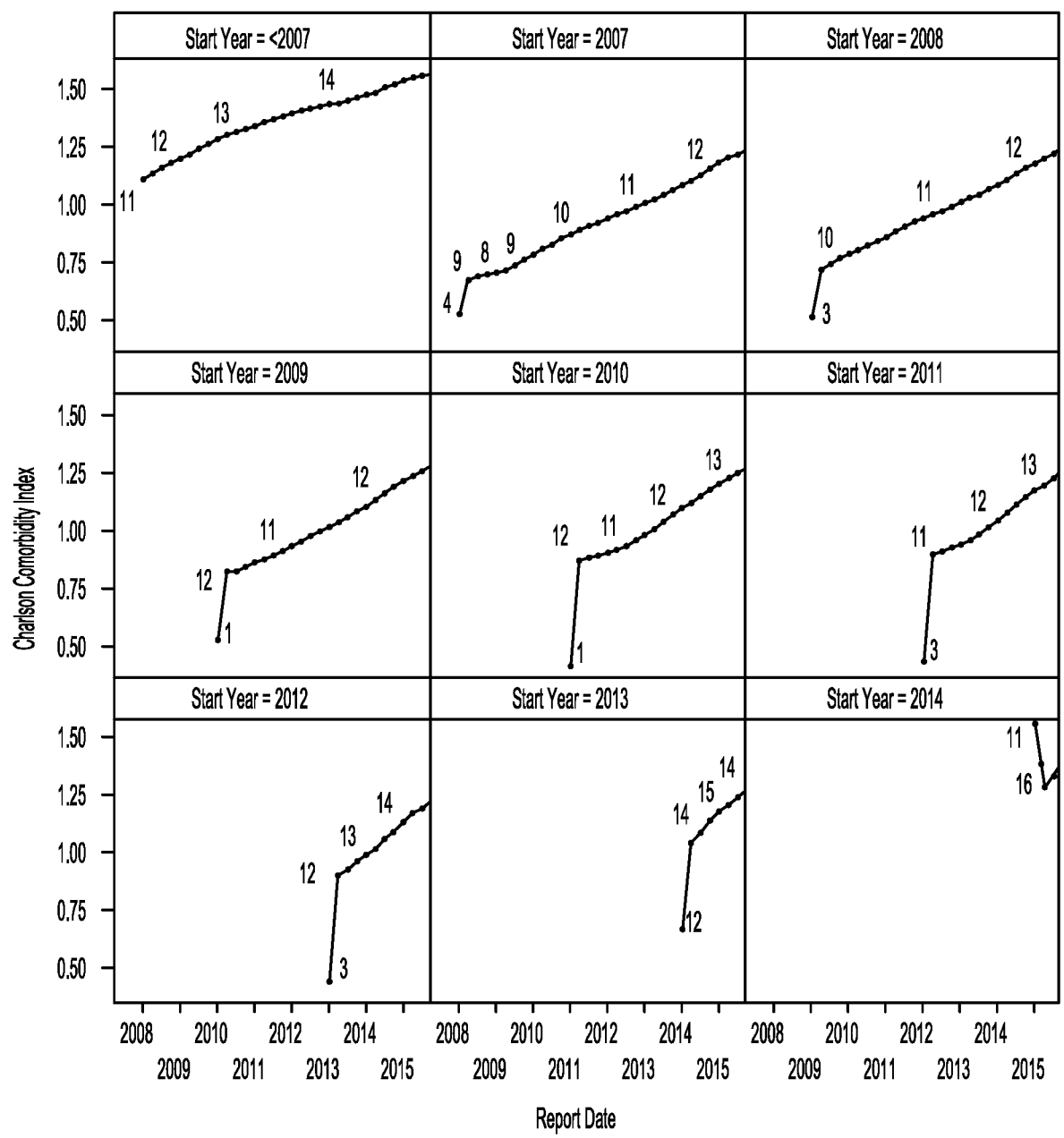
FIG. 11 shows an example quarterly plot of CCI by each cohort of start year

Although the overall positive association with the length of measurement period was not surprising, the low initial CCI in cohorts 2007-2012 warranted further investigation. The same calculation was repeated while fixing the measurement period to 365 days immediately before each quarterly date. In addition, it was hypothesized that the initial low CCI might be due to the artificially low utilization, as new patients gained familiarity with the VA healthcare system. Counts of 'I', 'O' in clinical setting substrings corresponding to each 365-day measurement period were obtained. These counts were proxy measurement for the extent of healthcare service. FIG. 11 shows the quarterly plot of CCI by each cohort of start year. Data labels are the median days of service utilization. For the cohorts 2007-2012, the initial utilization was dramatically lower.

Figure 12:
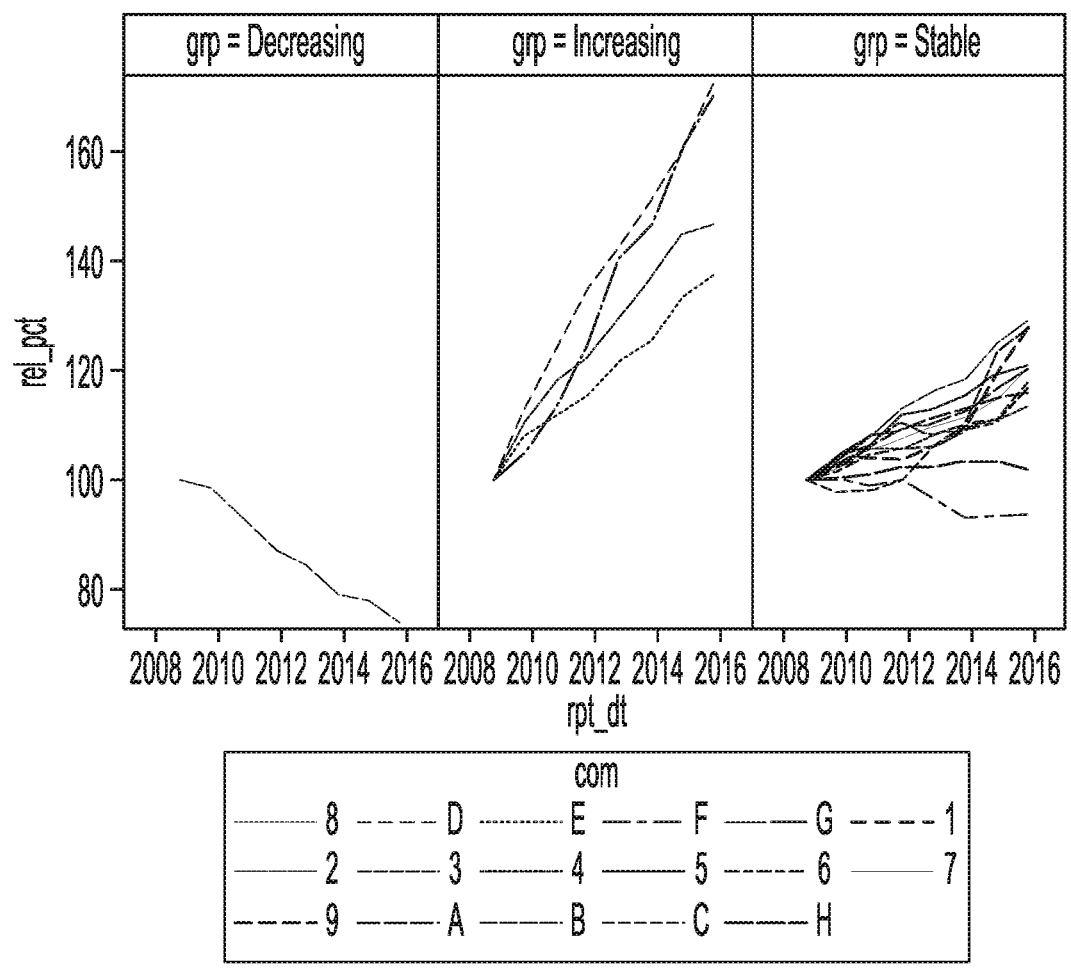
FIG. 12 shows an example relative change in proportion of comorbidity.

FIG. 12 is the relative change in proportion of comorbidity. Peptic ulcer disease decreases the fastest, while cancers, renal and liver diseases increase the fastest.

Figure 13:
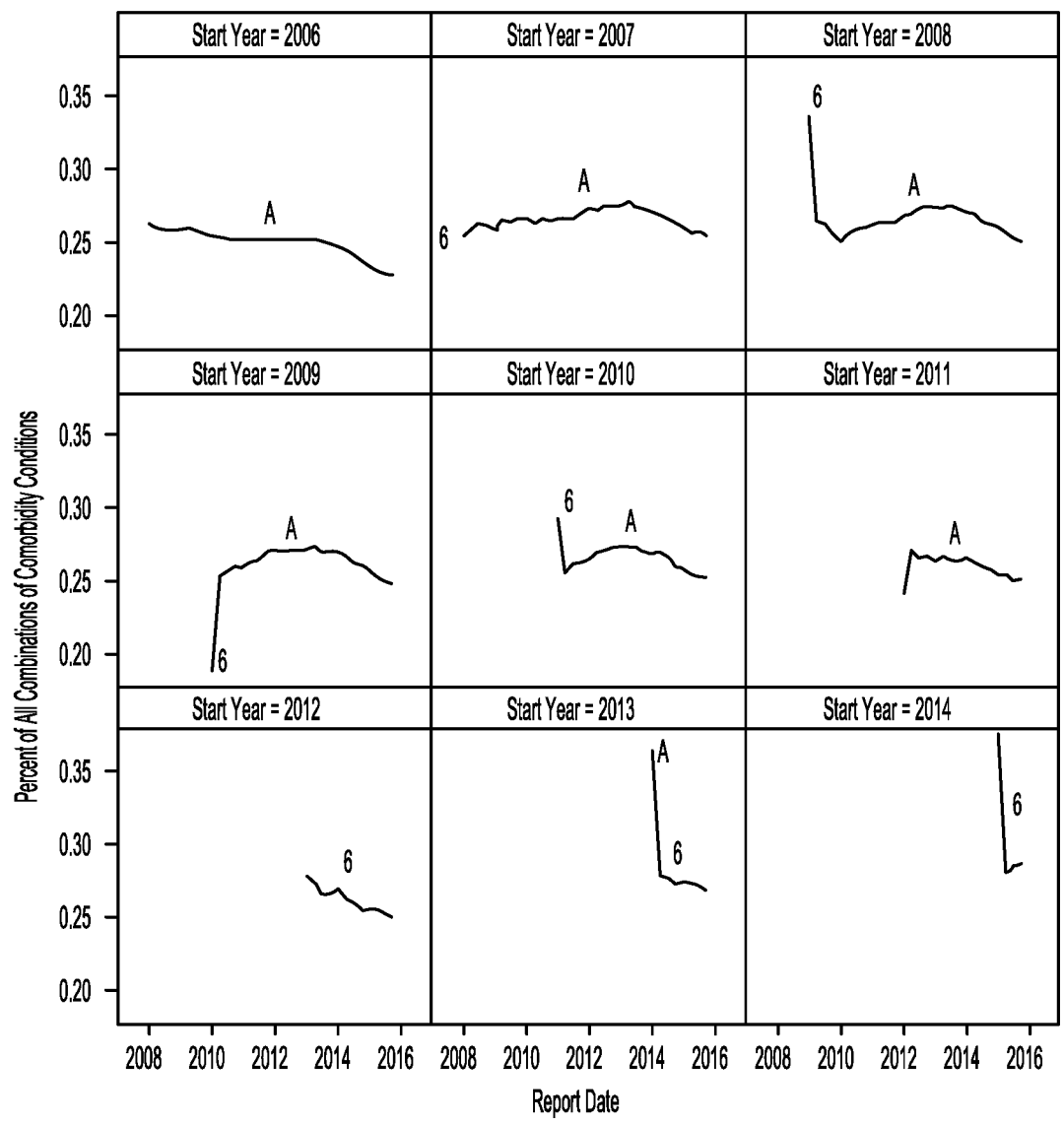
FIG. 13 shows an example of most common comorbidity over the years.

FIG. 13 shows the most common comorbidity over the years. Y-axis is the proportion of most frequent comorbidity over 365-day period. Diabetes was the most common comorbidity for earlier patients, while chronic pulmonary disease was the most common one for the more recent patients.

Different ARVs can be derived from the same set of clinical elements contained in the same source data. ARVs may provide different perspective from which to investigate research questions. For example, in a repeated measures study where one wishes to incorporate CCI as a covariate, one has the choice of including CCI as a fixed or time-varying covariate. Comorbidities highly correlated with other covariates might need to be excluded to improve model stability. As was demonstrated earlier, measurement period can influence CCI value. Sometime a minimum number of diagnoses are required before the comorbidity is confirmed. Creating each of these related variables from source data could be time consuming and data intensive. Researchers who plan to use the exact analysis variable typically repeat the same data preparation steps, simply due to different cohorts. The intermediate data object described herein, for example in the form of a text string, may be used to represent the history of a patient's medical information. The strings may be used to evaluate related ARVs and determine the most appropriate ARV for the investigation.

If more granular information is desired, such as different same-day comorbidities, additional symbols may be used along with mapping to retrieve the additional information. In an embodiment, strings for the same patient may have the same length and represent the same time period. This will allow derivation of ARVs from multiple strings to be more intuitive and easier. In another embodiment, information stored in different strings may be independent. This will allow more users with greater flexibility to create custom ARVs from the same set of strings.

The exemplary embodiments discussed above may be generalized by imputing a unique key to each position of a data array of symbols, e.g., a string of text characters, with each data array sharing at least a subset of the same imputed unique keys. For any unique key, each data array may provide an associated symbol responsive to that unique key to define a set of associated symbols that may be processed as an ARV linked to the imputed unique key. In an embodiment, the set of associated symbols may be a building block of many other building blocks derived from other sets of associated symbols for the ARVs. Any researcher may assemble subsets of these blocks in different ways for a wide range of ARVs. Multiple researchers may use these building blocks to form the same or different ARVs. There is great flexibility to researchers in constructing ARVs from the building blocks that may be formed from the same set of data arrays. Such building blocks are simpler and faster to use as the skills needed to identify and manipulate the building blocks are different from those needed to identify and define the data arrays.

In some of the examples discussed herein, each of the imputed unique keys corresponds to a calendar day. The symbols are disposed within the data structure in calendar sequence order with the strings thus representing a time-series of the occurrence or non-occurrence of events coded by the symbol(s) at that position in the string.

It is not required that the relationships be time-dependent events, that the symbols be disposed in a string in time-series order, that each symbol be limited to one text character, that all the symbols be text strings, or that all symbols be one character or have the same number of elements. Complexity of processing may increase with the complexity of content and arrangement of the data array.

One of these complexity features is to provide each symbol as an encoded collection of data elements for the associated imputed unique key for its position. For example, -continued $$\bullet g(x) = \begin{cases} \text{on medication,} & \text{if } x = 1 \\ \text{not on medication,} & \text{if } x = 0 \end{cases}$$

$$\bullet g^{-1}(y) = \begin{cases} 1 & \text{if } y = \text{on medication} \\ 0, & \text{if } y = \text{not on medication} \end{cases}$$

TABLE 4

| | | 1-on-1 Function Mapping between Natural Time to Entry Location in Sequence | | | |
|---|---|---|---|---|---|
| Entry Location in sequence | Natural Time | Sequence for Medication 1 Exposure | Sequence for Medication 2 Exposure | Sequence for Inpatient CPT Code | Lab A Result |
| k | t | $f_1(k) = t$<br>$f_1^{-1}(t) = k$ | $f_2(k) = t$<br>$f_2^{-1}(t) = k$ | $f_3(k) = t$<br>$f_3^{-1}(t) = k$ | $f_4(k) = t$<br>$f_4^{-1}(t) = k$ |
| | | 1-on-1 Function Obtaining Entry Value to Clinical Information | | | |
| Entry Value | Clinical Information | Sequence for Medication 1 Exposure | Sequence for Medication 2 Exposure | Sequence for Inpatient CPT Code | Lab A Result |
| x | y | $g_1(x) = y$<br>$g_1^{-1}(y) = x$ | $g_2(x) = y$<br>$g_2^{-1}(y) = x$ | $g_3(x) = y$<br>$g_3^{-1}(y) = x$ | $g_4(x) = y$<br>$g_4^{-1}(y) = x$ | when there are up to 16 different possible symbol interpretations for each data array position/unique key, an implementation may use hexadecimal data elements for each symbol. The encoded collection of data elements may comprise mapping information. The mapping information may represent a determination of information in terms of an intended unit. For instance, instead of strings of 0's and 1's, daily medication use could also be represented by a series of delimited numbers representing alternating run lengths of days on and off the medication. The encoded collection data elements may be associated with ARVs, TIAVs and the like and combinations thereof. The mapping information may be associated with mathematical functions. For example, the mapping information may be associated with an η(x) function or a g(x) function. As an example, a function may comprise the following: $x_k = f^{-1}(t)$. As another example, a function may comprise the following: $g(x_k = f^{-1}(t))$. Functions may be associated with an entry value, a location in a sequence, clinical information, or a time or other information and combinations thereof. Functions may be used to determine ARVs. Determining ARVs using functions may comprise several steps. For example, first determine $T=f_3(k)$ on CPT a sequence, for K where $x_k$ matches any of 36.0*–36.3*. Next, determine locations i's with $f\_2\hat{}(-1)$ (t) on medication 2 sequence, for all t's between T and T−30. Obtain values xi's and determine if any is 0. Then, determine locations j's=$f\_4\hat{}(-1)$ (t) on lab A sequence, for all t's between T and T−30. Obtain xj's and determine if any is <10. Finally, if step 2 and 3 both return True, then the value of ARV is T, else it's F. Functions may be simple or complex and may be determined or influenced by the design or construction of a sequence. Some example functions may comprise:

$$\bullet f(k) = \begin{cases} \text{start date,} & \text{if } k = 1 \\ \text{start date} + (k-1), & \text{if } k > 1 \end{cases}$$

$$\bullet f^{-1}(t) = \begin{cases} t - (\text{start date}) + 1 \end{cases}$$

Table 4, above, shows additional example functions.

The sequence data structure should be such that clinical information of every unit for each patient can be determined. For example, if day is the unit and clinical information is the ICD9 codes of outpatient visit, then one should be able to obtain the ICD9 codes for outpatient visit of a calendar date using appropriate f and g functions. The following is a conceptual picture of a sequence. Each cell is an entry location, not necessarily storing with a fixed number of bytes or characters. Assuming the intended unit is daily, there are 5 days of information in this sequence. An f function would tell me what calendar date each location is mapped to and vice versa, including day 2, 3, 5. A g function would tell me what the content (100, 200 . . . ) mean clinically, including the fact that day 2, 3, 5 have no information. They could be the exact clinical code like ICD9 or needs to be mapped (100=PTSD, 110=bipolar . . . ). Missing values need not be explicitly represented as shown. Missing values (as in Table 5) could be explicitly mapped as part of the function.

TABLE 5

| | Day (f function) | | | | |
|---|---|---|---|---|---|
| | 1 | 2 | 3 | 4 | 5 |
| Clinical Information (g function) | 100<br>110<br>131<br>420<br>121 | | | 500<br>200 | |

An additional example of a sequence of is shown in Table 6 wherein the top row indicates a k value and the bottom row indicates an x value. A k value may indicate temporal information, for instance a day in a series of days. Additionally, a k value may represent a location or position in a sequence. An x value may represent the occurrence or non-occurrence of an event.

TABLE 6

| k | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| value | | | | | | | | | | | | | | | | | | | | | | | | | |
| x | 0 | 0 | 0 | 0 | 0 | 0 | 0 | 0 | 0 | 1 | 1 | 1 | 1 | 1 | 1 | 1 | 1 | 0 | 0 | 0 | 1 | 1 | 1 | 1 | 1 |
| value | | | | | | | | | | | | | | | | | | | | | | | | | |

As an example, the above may be represented as ARVs as in Table 7 (below) where the value of $V_1$ designates a value of temporal information, for example, a day, and the value of $V_2$ designates a duration of an occurrence or non-occurrence of an event or a value representing consecutive occurrences or non-occurrences of an event. For example, in Table 7, the "8" found in the $V_2$ column represents the eight consecutive "1s" found in the bottom row of table 6 which start at 10 and continue through 17. Likewise, the "5" found in the $V_2$ column represents the five consecutive "1s" found in the bottom row of table 6 which start at 21 and continue through 25.

TABLE 7

| $V_1$ | $V_2$ |
|---|---|
| 10 | 8 |
| 21 | 5 |

When the data elements permit, such as when binary encoding is used, binary logic operations may be performed on the data arrays (e.g., intersection (AND), union (OR), inverse or negation, and the like).

One advantage for some implementations of the data arrays using one-character text strings is that many analysis and processing systems have efficient predefined string operators that may be used on these strings without requiring the advanced data extraction and cleaning skills used to construct the intermediate data objects themselves.

In some fields of endeavor, for example analysis of genetic data for particular patterns among extremely long data arrays, there are specialized data pattern analysis tools that may be applied to a collection of intermediate data objects of the present invention.

If not mentioned before, advantages of sharing just the set of data arrays allows greater data security as there is no opportunity for a researcher to access information not included in the intermediate data objects. Some of the database access security overhead is avoided by properly constructing and sharing limited intermediate data objects. Further, regulatory compliance (e.g., HIPPA) can be more easily enforced by masking/removing information in the intermediate data objects.

The efficiency of the intermediate data objects is not limited to the time needed to create ARVs but also in storage size. In the medication strings example, 3.4 GB of prescription-level data into 441 MB of string data. The size of the strings can be further compacted, for example using run-length encoding for strings having extended runs of the same symbol, for longer term storage and 'reconstituted' when needed.

Figure 14:
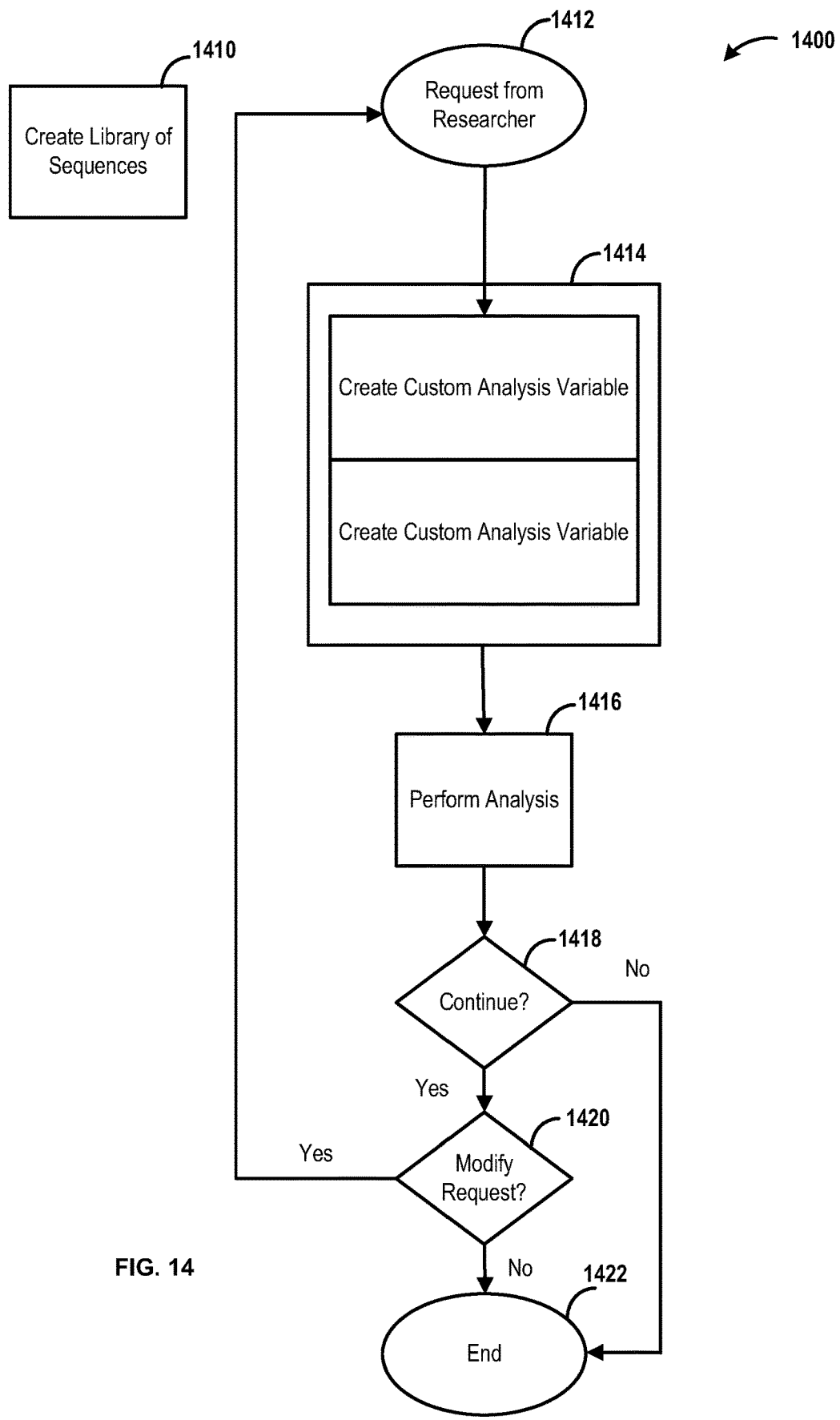
FIG. 14 shows an exemplary workflow.

FIG. 14 shows an example workflow 1400. In the workflow 1400, a library of sequences is created according to the methods described herein. A library of sequences is created at 1410 according to the methods described herein. At 1412 a researcher may make a request. At 1414, a custom analysis variable may be created according to the methods described herein. In some instances, more than one custom analysis variable may be created according to the methods described herein. One or more custom analysis variables may be created based on the library of sequences. At 1416, analysis may be performed. At 1418, a decision may be made as to whether or not to continue the workflow 1400. If the decision is made to continue, the workflow 1400 progresses to 1420 where a decision may be made as to whether or not to modify a request. If the decision is made to not continue, the workflow 1400 may progress to 1422 where in the workflow 1400 ends. If the decision is modify the request, the workflow 1400 may progress to 1412. If the decision is to not modify the request, the workflow 1400 may progress to 1422 where the workflow 1400 ends.

Figure 15:
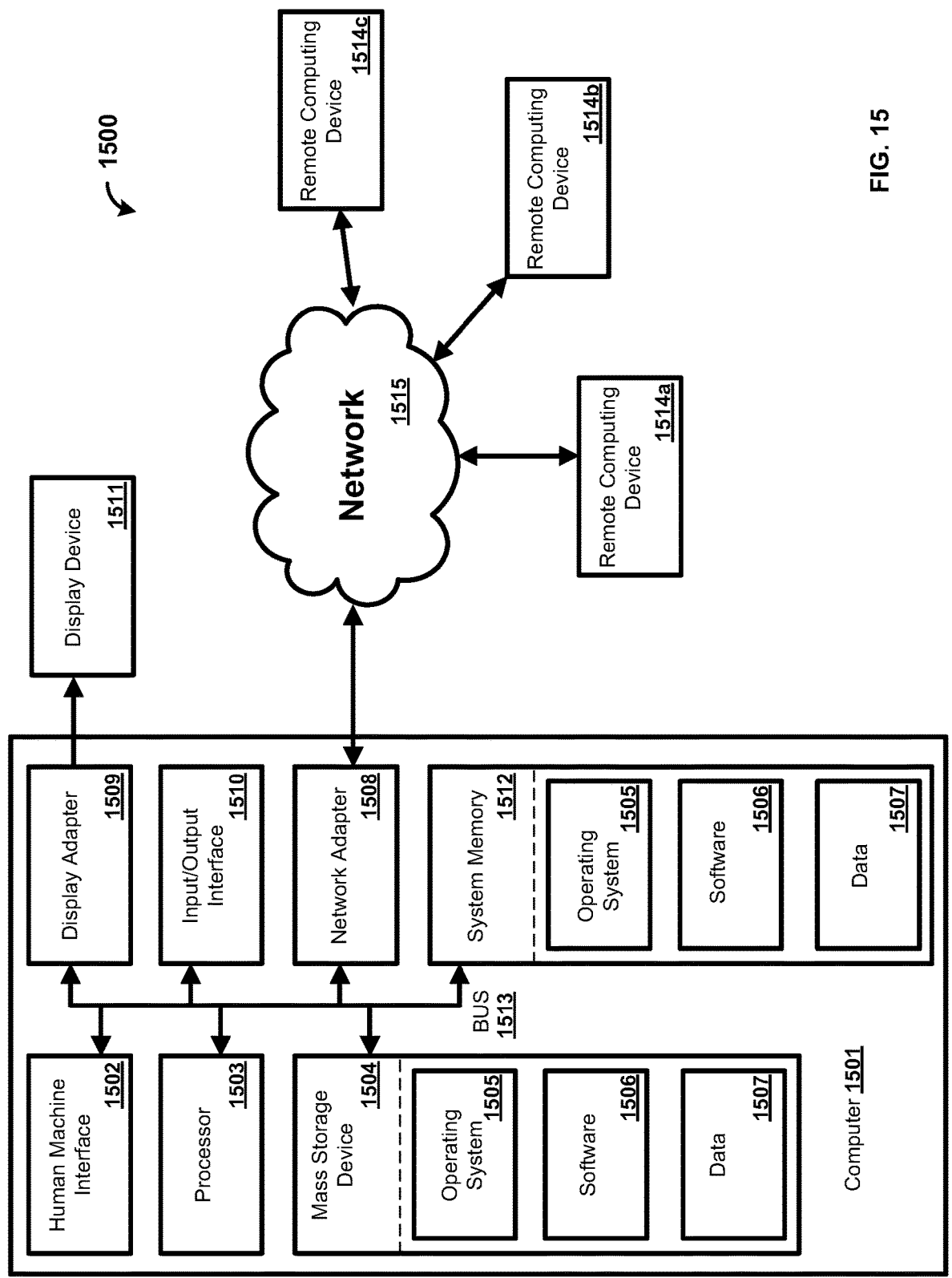
FIG. 15 shows a block diagram of an example computing device for implementing the disclosed methods.

FIG. 15 shows a system 1500 for intermediate data object generation and use. A computer 1501 may comprise one or more processors 1503, a system memory 1512, and a bus 1513 that couples various components of the computer 1501 including the one or more processors 1503 to the system memory 1512. In the case of multiple processors 1503, the computer 1501 may utilize parallel computing.

The bus 1513 may comprise one or more of several possible types of bus structures, such as a memory bus, memory controller, a peripheral bus, an accelerated graphics port, and a processor or local bus using any of a variety of bus architectures.

The computer 1501 may operate on and/or comprise a variety of computer readable media (e.g., non-transitory). Computer readable media may be any available media that is accessible by the computer 1501 and comprises, non-transitory, volatile and/or non-volatile media, removable and non-removable media. The system memory 1512 has computer readable media in the form of volatile memory, such as random access memory (RAM), and/or non-volatile memory, such as read only memory (ROM). The system memory 1512 may store data such as Data 1507 and/or program modules such as operating system 1505 and software 1506 that are accessible to and/or are operated on by the one or more processors 1503.

The computer 1501 may also comprise other removable/non-removable, volatile/non-volatile computer storage media. The mass storage device 1504 may provide non-volatile storage of computer code, computer readable instructions, data structures, program modules, and other data for the computer 1501. The mass storage device 1504 may be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules may be stored on the mass storage device 1504. An operating system 1505 and software 1506 may be stored on the mass storage device 1504. One or more of the operating system 1505 and software 1506 (or some combination thereof) may comprise program modules and the software 1506. Data 1507 may also be stored on the mass storage device 1504. Data 1507 may be stored in any of one or more databases known in the art. The databases may be centralized or distributed across multiple locations within the network 1515.

A user may enter commands and information into the computer 1501 via an input device (not shown). Such input devices comprise, but are not limited to, a keyboard, pointing device (e.g., a computer mouse, remote control), a microphone, a joystick, a scanner, tactile input devices such as gloves, and other body coverings, motion sensor, and the like These and other input devices may be connected to the one or more processors 1503 via a human machine interface 1502 that is coupled to the bus 1513, but may be connected by other interface and bus structures, such as a parallel port, game port, an IEEE 1394 Port (also known as a Firewire port), a serial port, network adapter 1508, and/or a universal serial bus (USB).

A display device 1511 may also be connected to the bus 1513 via an interface, such as a display adapter 1509. It is contemplated that the computer 1501 may have more than one display adapter 1509 and the computer 1501 may have more than one display device 1511. A display device 1511 may be a monitor, an LCD (Liquid Crystal Display), light emitting diode (LED) display, television, smart lens, smart glass, and/or a projector. In addition to the display device 1511, other output peripheral devices may comprise components such as speakers (not shown) and a printer (not shown) which may be connected to the computer 1501 via Input/Output Interface 1510. Any step and/or result of the methods may be output (or caused to be output) in any form to an output device. Such output may be any form of visual representation, including, but not limited to, textual, graphical, animation, audio, tactile, and the like. The display 1511 and computer 1501 may be part of one device, or separate devices.

The computer 1501 may operate in a networked environment using logical connections to one or more remote computing devices 1514a,b,c. A remote computing device 1514a,b,c may be a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device or other common network node, and so on. Logical connections between the computer 1501 and a remote computing device 1514a,b,c may be made via a network 1515, such as a local area network (LAN) and/or a general wide area network (WAN). Such network connections may be through a network adapter 1508. A network adapter 1508 may be implemented in both wired and wireless environments. Such networking environments are conventional and commonplace in dwellings, offices, enterprise-wide computer networks, intranets, and the Internet.

Application programs and other executable program components such as the operating system 1505 are shown herein as discrete blocks, although it is recognized that such programs and components may reside at various times in different storage components of the computing device 1501, and are executed by the one or more processors 1503 of the computer 1501. An implementation of software 1506 may be stored on or sent across some form of computer readable media. Any of the disclosed methods may be performed by processor-executable instructions embodied on computer readable media.

While specific configurations have been described, it is not intended that the scope be limited to the particular configurations set forth, as the configurations herein are intended in all respects to be possible configurations rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of configurations described in the specification.

It will be apparent to those skilled in the art that various modifications and variations may be made without departing from the scope or spirit. Other configurations will be apparent to those skilled in the art from consideration of the specification and practice described herein. It is intended that the specification and described configurations be considered as exemplary only, with a true scope and spirit being indicated by the following claims.

What is claimed is:

1. A method comprising:
    determining data values of a sequence of data stored in one or more databases supported on a stored program processing system, wherein the sequence of data comprises a series of values indicative of one or more occurrences or non-occurrences of an event obtained at successive times;
    generating an intermediate data structure associated with the event as a string of symbols, wherein each symbol of the string of symbols corresponds to at least one data value of the sequence of data;
    determining that each data value of the sequence of data indicates an occurrence of the event or a non-occurrence of the event;
    representing, in the string of symbols of the intermediate data structure, respective data values of the sequence of data that indicate the occurrence of the event with a first symbol; and
    representing, in the string of symbols of the intermediate data structure, respective data values of the sequence of data that indicate the non-occurrence of the event with a second symbol, wherein the intermediate data structure maintains an order of the first symbol and the second symbol based on the successive times of the sequence of data.

2. The method of claim 1, wherein generating the intermediate data structure associated with the event comprises generating a plurality of intermediate data structures, wherein each of the plurality of intermediate data structures is associated with a respective event.

3. The method of claim 1, further comprising:
    receiving a query, wherein the query comprises a time parameter and an event parameter;
    determining, based on the event parameter, that the query is related to the intermediate data structure; and
    determining, based on the time parameter, one or more first symbols or one or more second symbols in the string of symbols of the intermediate data structure.

4. The method of claim 3, wherein the time parameter comprises a time range that comprises a start time or date and an end time or date.

5. The method of claim 4, wherein determining, based on the time parameter, the one or more first symbols or the one or more second symbols in the string of symbols of the intermediate data structure comprises:
- determining a position in the string of symbols of the intermediate data structure corresponding to the start time or date;
- determining a position in the string of symbols of the intermediate data structure corresponding to the end time or date; and
- extracting the one or more first symbols or the one or more second symbols from the string of symbols of the intermediate data structure located between and including the position in the string of symbols of the intermediate data structure corresponding to the start time or date and the position in the string of symbols of the intermediate data structure corresponding to the end time or date.

6. A method comprising:
- determining data values of a sequence of data stored in one or more databases supported on a stored program processing system, wherein the sequence of data comprises a series of values indicative of one or more occurrences or non-occurrences of an event obtained at successive times; and
- generating an intermediate data structure,
- wherein the intermediate data structure comprises a string of symbols, wherein each symbol of the string of symbols corresponds to at least one data value of the sequence of data,
- wherein the string of symbols comprises one or more first symbols indicative of an occurrence of the event and one or more second symbols indicative of a non-occurrence of the event, wherein the string of symbols maintains an order of the one or more first symbols and the one or more second symbols based on the successive times of the sequence of data.

7. The method of claim 6, wherein generating the intermediate data structure comprises generating a plurality of intermediate data structures, wherein each of the plurality of intermediate data structures is associated with a respective event.

8. The method of claim 6, further comprising:
- receiving a query, wherein the query comprises a time parameter and an event parameter;
- determining, based on the event parameter, that the query is related to the intermediate data structure; and
- determining, based on the time parameter, the one or more first symbols or the one or more second symbols in the string of symbols of the intermediate data structure.

9. The method of claim 8, wherein the time parameter comprises a time range that comprises a start time or date and an end time or date.

10. The method of claim 9, wherein determining, based on the time parameter, the one or more first symbols or the one or more second symbols in the intermediate data structure comprises:
- determining a position in the istring of symbols of the ntermediate data structure corresponding to the start time or date;
- determining a position in the string of symbols of the intermediate data structure corresponding to the end time or date; and
- extracting the one or more first symbols or the one or more second symbols from the intermediate data structure located between and including the position in the string of symbols of the intermediate data structure corresponding to the start time or date and the position in the string of symbols of the intermediate data structure corresponding to the end time or date.

11. A computer readable medium comprising processor-executable instructions adapted to cause one or more computing devices to:
- determine data values of a sequence of data stored in one or more databases supported on a stored program processing system, wherein the sequence of data comprises a series of values indicative of one or more occurrences or non-occurrences of an event obtained at successive times;
- generate an intermediate data structure associated with the event as a string of symbols, wherein each symbol of the string of symbols corresponds to at least one data value of the sequence of data;
- determine that each data value of the sequence of data indicates an occurrence of the event or a non-occurrence of the event;
- represent, in the string of symbols of the intermediate data structure, respective data values of the sequence of data that indicate the occurrence of the event with a first symbol; and
- represent, in the string of symbols of the intermediate data structure, respective data values of the sequence of data that indicate the non-occurrence of the event with a second symbol, wherein the intermediate data structure maintains an order of the first symbol and the second symbol based on the successive times of the sequence of data.

12. The computer readable medium of claim 11, wherein generating the intermediate data structure associated with the event comprises generating a plurality of intermediate data structures, wherein each of the plurality of intermediate data structures is associated with a respective event.

13. The computer readable medium of claim 11, further comprising:
- receiving a query, wherein the query comprises a time parameter and an event parameter;
- determining, based on the event parameter, that the query is related to the intermediate data structure; and
- determining, based on the time parameter, one or more first symbols or one or more second symbols in the string of symbols of the intermediate data structure.

14. The computer readable medium of claim 13, wherein the time parameter comprises a time range that comprises a start time or date and an end time or date.

15. The computer readable medium of claim 14, wherein determining, based on the time parameter, the one or more first symbols or the one or more second symbols in the intermediate data structure comprises:
- determining a position in the string of symbols of the intermediate data structure corresponding to the start time or date;
- determining a position in the string of symbols of the intermediate data structure corresponding to the end time or date; and
- extracting the one or more first symbols or the one or more second symbols from the intermediate data structure located between and including the position in the string of symbols of the intermediate datastructure corresponding to the start time or date and the position in the string of symbols of the intermediate data structure corresponding to the end time or date.

16. A computer readable medium comprising processor-executable instructions adapted to cause one or more computing devices to:

determining data values of a sequence of data stored in one or more databases supported on a stored program processing system, wherein the sequence of data comprises a series of values indicative of one or more occurrences or non-occurrences of an event obtained at successive times; and generating an intermediate data structure, wherein the intermediate data structure comprises a string of symbols, wherein the string of symbols comprises one or more first symbols, indicative of an occurrence of the event and one or more second symbols indicative of a non-occurrence of the event, wherein the string of symbols maintains an order of the one or more first symbols and the one or more second symbols based on the successive times of the sequence of data.

17. The computer readable medium of claim 16, wherein generating the intermediate data structure comprises generating a plurality of intermediate data structures, wherein each of the plurality of intermediate data structures is associated with a respective event.

18. The computer readable medium of claim 17, further comprising:
receiving a query, wherein the query comprises a time parameter and an event parameter;
determining, based on the event parameter, that the query is related to the intermediate data structure; and
determining, based on the time parameter, the one or more first symbols or the one or more second symbols in the string of symbols of the intermediate data structure.

19. The computer readable medium of claim 18, wherein the time parameter comprises a time range comprising a start time or date and an end time or data, wherein determining, based on the time parameter, the one or more first symbols or the one or more second symbols in the intermediate data structure comprises:
determining a position in the string of symbols of the intermediate data structure corresponding to the start time or date;
determining a position in the string of symbols of the intermediate data structure corresponding to the end time or date; and
extracting the one or more first symbols or the one or more second symbols from the intermediate data structure located between and including the position in the string of symbols of the intermediate data structure corresponding to the start time or date and the position in the string of symbols of the intermediate data structure corresponding to the end time or date.

20. A method comprising:
determining, based on state-based data stored in one or more databases supported on a stored program processing system, time-stamped data;
determining, based on the time-stamped data stored in the one or more databases supported on the stored program processing system, a subset of the time-stamped data;
determining, based on the subset of the time-stamped data, a subset of the state-based data;
determining, based on the subset of the state-based data, a sequence of the subset of the state-based data; and
storing the sequence of the subset of the state-based data as at least one string of symbols in one or more symbolic data structures, wherein the subset of the state-based data is preserved within the at least one string of symbols of the one or more symbolic data structures, wherein the at least one string of symbols comprises one or more first symbols indicative of an occurrence of an event within the state-based data and one or more second symbols indicative of a non-occurrence of the event within the state-based data, wherein the at least one string of symbols maintains an order of the one or more first symbols and the one or more second symbols based on the subset of the state-based data.

21. The method of claim 20, wherein the state-based data comprises at least one of a medical condition of one or more persons, a medical treatment of one or more persons, or a medical diagnosis of one or more persons, or combinations thereof.

22. The method of claim 21, wherein the symbolic data structures comprises at least one state-based data associated with a particular member of a population.

23. The method of claim 20, wherein the at least one string of symbols maps to at least a portion of the state-based data.

24. The method of claim 20, wherein the time-stamped data comprises temporal information, wherein the temporal information is associated with the state-based data.

25. The method of claim 20, wherein the time-stamped data comprises at least one electronic health record, and wherein the at least one electronic health record is stored in a database comprising a plurality of tables.

* * * * *